(12) United States Patent
Zhao et al.

(10) Patent No.: US 9,556,155 B2
(45) Date of Patent: *Jan. 31, 2017

(54) METHODS OF TREATING FATTY LIVER DISEASE

(71) Applicant: Genzyme Corporation, Cambridge, MA (US)

(72) Inventors: Hongmei Zhao, Southborough, MA (US); Nelson S. Yew, West Upton, MA (US); Seng H. Cheng, Natick, MA (US); Canwen Jiang, Southborough, MA (US); Cynthia Marie Arbeeny, Marlborough, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,732

(22) Filed: Apr. 8, 2014

(65) Prior Publication Data

US 2015/0051261 A1 Feb. 19, 2015

Related U.S. Application Data

(63) Continuation of application No. 12/227,076, filed as application No. PCT/US2007/068521 on May 9, 2007, now Pat. No. 8,716,327.

(60) Provisional application No. 60/746,811, filed on May 9, 2006.

(51) Int. Cl.
| | |
|---|---|
| *A61K 31/40* | (2006.01) |
| *C07D 405/06* | (2006.01) |
| *A61K 31/395* | (2006.01) |
| *A61K 31/4245* | (2006.01) |
| *A61K 31/4025* | (2006.01) |
| *A61K 45/06* | (2006.01) |

(52) U.S. Cl.
CPC ........... *C07D 405/06* (2013.01); *A61K 31/395* (2013.01); *A61K 31/40* (2013.01); *A61K 31/4025* (2013.01); *A61K 31/4245* (2013.01); *A61K 45/06* (2013.01)

(58) Field of Classification Search
CPC .............................. A61K 31/395; A61K 31/40
USPC ................................................. 514/422, 408
See application file for complete search history.

(56) References Cited

U.S. PATENT DOCUMENTS

| | | | |
|---|---|---|---|
| 4,065,562 A | 12/1977 | Ohata et al. | |
| 4,182,767 A | 1/1980 | Murai et al. | |
| 4,533,668 A | 8/1985 | Matsumura et al. | |
| 4,639,436 A | 1/1987 | Junge et al. | |
| 5,041,441 A | 8/1991 | Radin et al. | |
| 5,302,609 A | 4/1994 | Shayman et al. | |
| 5,472,969 A | 12/1995 | Platt et al. | |
| 5,525,616 A | 6/1996 | Platt et al. | |
| 5,631,394 A | 5/1997 | Wei et al. | |
| 5,707,649 A | 1/1998 | Inokuchi et al. | |
| 5,763,438 A | 6/1998 | Inokuchi et al. | |
| 5,849,326 A | 12/1998 | Inokuchi et al. | |
| 5,907,039 A | 5/1999 | Jinbo et al. | |
| 5,916,911 A | 6/1999 | Shayman et al. | |
| 5,945,442 A | 8/1999 | Shayman et al. | |
| 5,952,370 A | 9/1999 | Shayman et al. | |
| 5,972,928 A | 10/1999 | Chatterjee | |
| 6,030,995 A | 2/2000 | Shayman et al. | |
| 6,040,332 A | 3/2000 | Shayman et al. | |
| 6,051,598 A | 4/2000 | Shayman et al. | |
| 6,228,889 B1 | 5/2001 | Chatterjee | |
| 6,255,336 B1 | 7/2001 | Shayman et al. | |
| 6,335,444 B1 | 1/2002 | Jimbo et al. | |
| 6,407,064 B2 | 6/2002 | Masuda et al. | |
| 6,511,979 B1 | 1/2003 | Chatterjee | |
| 6,569,889 B2 | 5/2003 | Shayman et al. | |
| 6,610,703 B1 | 8/2003 | Jacob et al. | |
| 6,660,749 B2 | 12/2003 | Butters et al. | |
| 6,835,831 B2 | 12/2004 | Hirth | |
| 6,855,830 B2 | 2/2005 | Hirth et al. | |
| 6,890,949 B1 | 5/2005 | Shayman et al. | |
| 6,916,802 B2 | 7/2005 | Shayman et al. | |
| 7,148,251 B2 | 12/2006 | Shayman | |
| 7,196,205 B2 | 3/2007 | Siegel et al. | |
| 7,253,185 B2 | 8/2007 | Shayman et al. | |
| 7,265,228 B2 | 9/2007 | Hirth et al. | |
| 7,335,681 B2 | 2/2008 | Shayman et al. | |
| 7,615,573 B2 | 11/2009 | Siegel et al. | |
| 7,763,738 B2 | 7/2010 | Hirth et al. | |
| 8,003,617 B2 | 8/2011 | Cheng et al. | |
| 8,304,447 B2 | 11/2012 | Siegel et al. | |
| 8,309,593 B2 | 11/2012 | Siegel et al. | |
| 8,389,517 B2 | 3/2013 | Ibraghimov-Beskrovnaya et al. | |
| 8,716,327 B2 | 5/2014 | Zhao et al. | |

(Continued)

FOREIGN PATENT DOCUMENTS

| | | |
|---|---|---|
| EA | 007395 | 10/2006 |
| EP | 126974 | 12/1984 |

(Continued)

OTHER PUBLICATIONS

Final Office Action for U.S. Appl. No. 14/595,251, titled: "2-Acylaminopropoanol-Type Glucosylceramide Synthase Inhibitors" Dated Mailed: May 5, 2015.

(Continued)

*Primary Examiner* — Shengjun Wang

(74) *Attorney, Agent, or Firm* — Hamilton, Brook, Smith & Reynolds, P.C.

(57) ABSTRACT

The disclosure provides methods for treating fatty liver disease and associated conditions by inhibiting the synthesis of glucosphingolipids, as exemplified by the use of glucosylceramide synthase substrate analogs.

34 Claims, 7 Drawing Sheets

(56) References Cited

U.S. PATENT DOCUMENTS

| | | |
|---|---|---|
| 8,729,075 B2 | 5/2014 | Ibraghimov-Beskrovnaya et al. |
| 8,912,177 B2 | 12/2014 | Ibraghimov-Beskrovnaya et al. |
| 8,940,776 B2 | 1/2015 | Siegel et al. |
| 9,272,996 B2 | 3/2016 | Siegel et al. |
| 2001/0003741 A1 | 6/2001 | Masuda et al. |
| 2002/0156107 A1 | 10/2002 | Shayman et al. |
| 2002/0198240 A1 | 12/2002 | Shayman et al. |
| 2003/0050299 A1 | 3/2003 | Hirth et al. |
| 2003/0073680 A1 | 4/2003 | Shayman et al. |
| 2004/0260099 A1 | 12/2004 | Shayman |
| 2005/0009872 A1 | 1/2005 | Hirth et al. |
| 2005/0049235 A1 | 3/2005 | Shayman et al. |
| 2005/0222244 A1 | 10/2005 | Siegel et al. |
| 2005/0239862 A1 | 10/2005 | Shayman et al. |
| 2005/0267094 A1 | 12/2005 | Shayman et al. |
| 2006/0058349 A1 | 3/2006 | Ali et al. |
| 2006/0074107 A1 | 4/2006 | Butters et al. |
| 2006/0217560 A1 | 9/2006 | Shayman |
| 2007/0025965 A1 | 2/2007 | Lobb |
| 2007/0066581 A1 | 3/2007 | Aerts |
| 2007/0072916 A1 | 3/2007 | Shayman |
| 2007/0112028 A1 | 5/2007 | Orchard |
| 2007/0203223 A1 | 8/2007 | Siegel et al. |
| 2008/0146533 A1 | 6/2008 | Shayman et al. |
| 2008/0171874 A1 | 7/2008 | Berger et al. |
| 2009/0312392 A1 | 12/2009 | Shayman et al. |
| 2010/0256216 A1 | 10/2010 | Siegel et al. |
| 2010/0298317 A1 | 11/2010 | Natoli et al. |
| 2011/0166134 A1 | 7/2011 | Ibraghimov-Beskrovnaya et al. |
| 2011/0184021 A1 | 7/2011 | Siegel et al. |
| 2012/0022126 A1 | 1/2012 | Cheng et al. |
| 2012/0322786 A1 | 12/2012 | Siegel et al. |
| 2012/0322787 A1 | 12/2012 | Siegel et al. |
| 2013/0225573 A1 | 8/2013 | Ibraghimov-Beskrovnaya et al. |
| 2014/0336174 A1 | 11/2014 | Ibraghimov-Beskrovnaya et al. |
| 2015/0190373 A1 | 7/2015 | Cheng et al. |
| 2015/0216872 A1 | 8/2015 | Natoli et al. |
| 2015/0225393 A1 | 8/2015 | Siegel et al. |

FOREIGN PATENT DOCUMENTS

| | | |
|---|---|---|
| EP | 0 144 290 A | 6/1985 |
| EP | 0765865 A1 | 4/1997 |
| EP | 1 384 719 A1 | 1/2004 |
| EP | 1 528056 | 5/2005 |
| EP | 1 576 894 A1 | 9/2005 |
| GB | 2054371 | 2/1981 |
| JP | 35-5798 | 5/1960 |
| JP | S60136595 A | 7/1985 |
| JP | 9-169664 | 6/1997 |
| JP | 9216856 A1 | 8/1997 |
| JP | 10-324671 | 12/1998 |
| JP | 10338636 A | 12/1998 |
| JP | 2001-226362 | 8/2001 |
| JP | 2003-238410 | 8/2003 |
| WO | WO 97/10817 | 3/1997 |
| WO | WO 98/52553 | 11/1998 |
| WO | WO 01/04108 A1 | 1/2001 |
| WO | WO 01/54654 A2 | 8/2001 |
| WO | WO 01/80852 A1 | 11/2001 |
| WO | WO 02/50019 A2 | 6/2002 |
| WO | WO 02/055498 | 7/2002 |
| WO | WO 02/062777 A2 | 8/2002 |
| WO | WO 03/008399 | 1/2003 |
| WO | WO 03/057874 | 7/2003 |
| WO | WO 03/068255 A1 | 8/2003 |
| WO | WO 2004/007453 | 1/2004 |
| WO | WO 2004/056748 A1 | 7/2004 |
| WO | WO 2004/078193 A1 | 9/2004 |
| WO | WO 2005/039578 A2 | 5/2005 |
| WO | WO 2005/040118 A1 | 5/2005 |
| WO | WO 2005/063275 | 7/2005 |
| WO | WO 2005/068426 A1 | 7/2005 |
| WO | WO 2005/087023 A1 | 9/2005 |
| WO | WO 2005/108600 A1 | 11/2005 |
| WO | WO 2005/123055 | 12/2005 |
| WO | WO2006/023827 | 3/2006 |
| WO | WO 2006/053043 A2 | 5/2006 |
| WO | WO 2006/053043 A3 | 5/2006 |
| WO | WO 2006/081276 A1 | 8/2006 |
| WO | WO 2007/022518 A2 | 2/2007 |
| WO | WO 2007/134086 A2 | 11/2007 |
| WO | WO 2007/134086 A3 | 11/2007 |
| WO | WO 2008/011478 | 1/2008 |
| WO | WO 2008/011487 | 1/2008 |
| WO | WO 2008/012555 | 1/2008 |
| WO | WO 2008/024337 A2 | 2/2008 |
| WO | WO 2008/097673 A1 | 8/2008 |
| WO | WO 2008/150486 A2 | 12/2008 |
| WO | WO 2009/045503 | 4/2009 |
| WO | WO 2009/117150 | 9/2009 |

OTHER PUBLICATIONS

Non-Final Office Action for U.S. Appl. No. 14/464,432, titled: "Method of Treating Diabetes Mellitus" Date Mailed: Sep. 9, 2015.
Non-Final Office Action for U.S. Appl. No. 13/595,251, titled: "2-Acylaminopropoanol-Type Glucosylceramide Synthase Inhibitors" Date Mailed: Nov. 19, 2014.
Non-Final Office Action for U.S. Appl. No. 14/255,634, titled: "Glucosylceramide Synthase Inhibition for the Treatment of Collapsing Glomerulopathy and Other Glomerular Disease" Date Mailed: Aug. 11, 2015.
Notice of Allowance and Fee(s) Due for U.S. Appl. No. 13/595,251; titled: "2-Acylaminopropoanol-Type Glucosylceramide Synthase Inhibitors" Date Mailed: Oct. 21, 2015.
Deshmukh, G.D., et al., "Abnormalities of glycosphingolipid, sulfatide, and ceramide in the Polycystic (cpk/cpk) mouse", Journal of Lipid Research, 35: 1611-1618 1994).
Extended European Search Report for European Application No. EP 15 16 2842, "Methods of Treating Fatty Liver Disease", Date of completion: Jul. 24, 2015.
Grcevska, L., et al., "Treatment with Steroids and Cyclophoshamide in Collapsing Glomerulopathy and Focal Segmental Glomerulosclerosis-Comparative Study" Nephrology Dialysis Transplantation, Oxford University Press, GB, 15(9): A89, XP008047905, ISSN: 0931-0509.
Huynh-Do, U., "Membranous nephropathy: Pathogenesis, diagnostics and current treatment", Der Nephrologe; Zeitschrift Für Nephrologie Und Hypertensiologie, Springer, Berlin, DE, 2(1): 20-26 (Jan. 1, 2007).
Klein, M., et al., "Cyclosporine Treatment of Glomerular Diseases", Annu. Rev. Med, 17 pgs. (Feb. 1, 1999).
Mok, C., et al., "Long-term Outcome of Diffuse Proliferative Lupus Glomerulonephritis Treated with Cyclophosphamide", American Journal of Medicine, 119(4):355e.25-355e33 (Apr. 1, 2006).
Notice of Allowance and Fee(s) Due for U.S. Appl. No. 12/681,291; titled: "Method of Treating Polycystic Kidney Diseases With Ceramide Derivatives" Date Mailed: Aug. 4, 2014.
Notice of Allowance and Fee(s) Due for U.S. Appl. No. 13/595,349; titled: "2-Acylaminopropoanol-Type Glucosylceramide Synthase Inhibitors" Date Mailed: Sep. 10, 2014.
Final Office Action for U.S. Appl. No. 12/227,076, ; titled: "Methods of Treating Fatty Liver Disease" dated Mar. 20, 2012.
Non-Final Office Action for U.S. Appl. No. 12/227,076, ; titled: "Methods of Treating Fatty Liver Disease", mailed on Nov. 23, 2011.
Non-Final Office Action for U.S. Appl. No. 12/681,291 dated Dec. 10, 2012, "Method of Treating Polycystic Kidney Diseases with Ceramide Derivatives".
Non-Final Office Action for U.S. Appl. No. 13/122,135, titled "2-Acylaminopropoanol-Type Glucosylceramide Synthase Inhibitors" mailed on Apr. 27, 2012.
Non-Final Office for U.S. Appl. No. 12/681,291, titled "Method of Treating Polycystic Kidney Diseases with Ceramide Derivatives", dated: Oct. 18, 2013.
Non-Final Office for U.S. Appl. No. 13/193,990, titled "Method of Treating Diabetes Mellitus", dated: Feb. 20, 2014.

(56) References Cited

OTHER PUBLICATIONS

Non-Final Office for U.S. Appl. No. 13/595,349, titled "2-Acylaminopropoanol-Type Glucosylceramide Synthase Inhibitors", dated: Dec. 19, 2013.
Notice of Allowance and Fee(s) Due for U.S. Appl. No. 11/667,224, titled: "Method of Treating Diabetes Mellitus" Date Mailed: Apr. 22, 2011.
Notice of Allowance and Fee(s) Due for U.S. Appl. No. 12/227,076; titled: "Methods of Treating Fatty Liver Disease" Date Mailed: Oct. 9, 2012.
Notice of Allowance and Fee(s) Due for U.S. Appl. No. 12/227,076; titled: "Methods of Treating Fatty Liver Disease" Date Mailed: Jun. 4, 2013.
Notice of Allowance and Fee(s) Due for U.S. Appl. No. 12/227,076; titled: "Methods of Treating Fatty Liver Disease" Date Mailed: Dec. 23, 2013.
Notice of Allowance and Fee(s) Due for U.S. Appl. No. 12/601,871; "2-Acylaminopropoanol-Type Glucosylceramide Synthase Inhibitors" Date Mailed: Aug. 9, 2012.
Notice of Allowance and Fee(s) Due for U.S. Appl. No. 13/055,036; titled: "Glucosylceramide Synthase Inhibition for the Treatment of Collapsing Glomerulopathy and Other Glomerular Disease" Date Mailed: Oct. 31, 2012.
Notice of Allowance and Fee(s) Due for U.S. Appl. No. 13/122,135; "2-Acylaminopropoanol-Type Glucosylceramide Synthase Inhibitors" Date Mailed: Aug. 1, 2012.
Notice of Allowance and Fee(s) Due for U.S. Appl. No. 13/762,102; titled: "Glucosylceramide Synthase Inhibition for the Treatment of Collapsing Glomerulopathy and Other Glomerular Disease" Date Mailed: Jan. 9, 2014.
Office Action dated Mar. 29, 2012 for U.S. Appl. No. 12/601,871, titled: "2-Acylaminopropoanol-Type Glucosylceramide Synthase Inhibitors".
Office Action dated May 28, 2013 for U.S. Appl. No. 13/762,102; titled: "Glucosylceramide Synthase Inhibition for the Treatment of Collapsing Glomerulopathy and Other Glomerular Disease".
Office Action for U.S. Appl. No. 12/601,871, titled: "2-Acylaminopropoanol-Type Glucosylceramide Synthase Inhibitors" dated Sep. 21, 2011.
Abdel-Magid, A., et al., "Metal-Assisted Aldol Condensation of Chiral a-Halogenated Imide Enolates: A Stereocontrolled Chiral Epoxide Synthesis[1]," *J. Am. Chem Soc.*, 108: 4595-4602 (1986).
Abe, A., et al., "Improved Inhibitors of Glucosylceramide Synthase[1]," *J. Biochem.*, 111: 191-196 (1992).
Abe, A., et al., "Induction of glucosylceramide synthase by synthase inhibitors and ceramide," *Biochimics Biophysica Acta*, 1299: 333-341 (1996).
Abe, A., et al., "Metabolic effects of short-chain ceramide and glucosylceramide on sphingolipids and protein kinase C," *Eur. J. Biochem*, 210: 765-773 (1992).
Abe, A., et al., "Reduction of Globotriasylceramide in Fabry Disease mice by substrate deprivation", *J. Clin Invest.* 105(11): 1563-1571, Jun. 2000.
Abe, A., et al., "Structural and stereochemical studies of potent inhibitors of glucosylceramide synthase and tumor cell growth," *J. Lipid Research*, 36: 611-621 (1995).
Abe, A., et al., "Use of Sulfobutyl Ether β-Cyclodextrin as a Vehicle for *d-threo*-1-Phenyl-2-decanoylamino-3-morpholinopropanol-Related Glucosylceramide Synthase Inhibitors", *Analytical Biochemistry*, vol. 287, pp. 344-347 (2000).
Adams, L.A., et al. "Nonalcoholic fatty liver disease", *CMAJ*, 172(7):899-905 (2005).
Alberti, C., et al., "Chloramphenicol. XII and XIII. Chloramphenicol analogs. p-Nitrophenyldiaminopropanols", *Chemical Abstracts Service*, XP002495477 retrieved from CAPLUS Database accession No. 1957:17088 (abstract).
Alker, D., et al., "Application of Enantiopure Templated Azomethine Ylids to β-Hydroxy-a-amino Acid Synthesis," *Tetrahedron: Asymmetry*, 54: 6089-6098 (1998).

Alon, R., et al., "Glycolipid Ligands for Selectins Support Leukocyte Tethering and Rolling Under Physiologic Flow Conditions[1]," *J. Immunol.*, 154: 5356-5366 (1995).
Ames, Bruce N., "Assay of Inorganic Phosphate, Total Phosphate and Phosphatases," *Methods Enzymol.*, 8: 115-118 (1996).
Asano, N., "Glycosidase Inhibitors: update and perspectives on practical use", *Glycobiology*, 13(10):93R-104R (2003).
Belikov., V.G., "Pharmaceutical Chemistry, Moscow", *Vysshaya Shkola Publishers*, pp. 43-47 (1993).
Bielawska, A., et al.., "Ceramide-mediated Biology: Determination of Structural and Stereospecific Requirements Through the Use of N-Acyl-Phenylaminoalcohol Analogs," *J. Biol. Chem.*, 267: 18493-18497 (1992).
Bielawska, et al., "Modulation of cell growth and differentiation by ceramide," *FEBS Letters*, 307(2): 211-214 (1992).
Blobe, G.C., et al., "Regulation of protein kinase C and its role in cancer biology," *Cancer Metastasis Rev.*, 13: 411-431 (1994).
Brenkert, A., et al., "Synthesis of Galactosyl Ceramide and Glucosyl Ceramide by Rat Brain: Assay Procedures and Changes with Age," *Brain Res.*, 36: 183-193 (1972).
CAPLUS Listing of Accession No. 1985:221199, Keith McCullagh, et al., "Carboxyalkyl peptide derivatives."
Carson, K.G., et al., "Studies on Morpholinosphingolipids: Potent Inhibitors of Glucosylceramide Synthase," *Tetrahedron Letters*, 35(17): 2659-2662 (1994).
Chatterjee, S., et al.,"Oxidized low density lipoprotein stimulates aortic smooth muscle cell proliferation", *Glycobiology*, 6(3): 303-311, 1996.
Chatterjee, S., et al.,"Role of lactosylceramide and MAP kinase in the proliferation of proximal tubular cells in human polycystic kidney disease", *Journal of Lipid Research*, 37(6): 1334-1344 (1996).
Clark, J.M., et al., "Nonalcoholic Fatty Liver Disease: An Underrecognized Cause of Cryptogenic Cirrhosis", *JAMA* 289(22): 3000-3004 (2003).
Comuzzie, A.G., et al., "The Baboon as a Nonhuman Primate Model for the Study of the Genetics of Obesity", *Obesity Research*, 11(1):75-80 (2003).
Dellaria, Jr., J.F., et al., "Enantioselective Synthesis of a-Amino Acid Derivatives via the Stereoselective Alkylation of a Homochiral Glycin Enolate Synthon[1]," *J. Org. Chem.*, 54: 3916-3926 (1989).
Dickie, P., et al., "HIV-Associated Nephropathy in Transgenic Mice Expressing HIV-1 Genes," *Virology*, 185:109-119, 1991.
Dittert, L.W., et al., "Acetaminophen Prodrugs I—Synthesis, Physicochemical Properties and Analgesic Activity", *J. Pharm. Sci.* 57(5), pp. 774-780 (1968).
Elbein, A.D., "Glycosidase inhibitors: inhibitors of N-linked oligosaccharide processing" *The FASEB Journal*, 5: 3055-3063 (1991).
European Search Report for EP Patent Application No. 12007327.5, "Method of Treating Polycystic Kidney Diseases With Ceramide Derivatives" dated Apr. 11, 2013.
European Search Report, European Application No. 09003291.3, titled: "Synthesis of UDP-Glucose: N-Acylsphingosine Glucosyl-Transferase Inhibitors" Apr. 29, 2009.
European Search Report, European Application No. 13154949.5, "2-Acylaminopropoanol-Type Glucosylceramide Synthase Inhibitors" dated Jul. 12, 2013.
European Search Report, European Application No. 13154955.2, "2-Acylaminopropoanol-Type Glucosylceramide Synthase Inhibitors" dated Jul. 10, 2013.
European Search Report, European Application No. 13154967.7, "2-Acylaminopropoanol-Type Glucosylceramide Synthase Inhibitors" dated Jul. 18, 2013.
European Search Report, European Application No. 13154970.1, "2-Acylaminopropoanol-Type Glucosylceramide Synthesis Inhibitors" dated Jul. 10, 2013.
Evans, D.A., et al., "Stereoselective Aldol Condensations via Boron Enolates[1]," *J. Am. Chem. Soc.*, 103: 3099-3111 (1981).
Fan, J-G., et al., "Preventie Effects of Metformin on Rats with nonalcoholic stcatohcpatitis", *Hepatology*, 34(4)(1), p. 501A (2003).

(56) References Cited

OTHER PUBLICATIONS

Felding-Habermann, B., et al., "A Ceramide Analog Inhibits T Cell Proliferative Response through Inhibition of Glycosphingolipid Synthesis and Enhancement of N,N-Dimethylsphingosine Synthesis," *Biochemistry*, 29: 6314-6322 (1990).

Folch, J., et al., "A Simple Method for the Isolation and Purification of Total Lipides from Animal Tissues", *J. Biol. Chem.*, 226:497-509, 1956.

Freireich, E., et al., "Quantitative Comparison of Toxicity of Anticancer Agents in Mouse, Rat, Hampster, Dog, Monkey, and Man[1,2]", *Cancer Chemother. Reports* 50(4):219 (1996).

Gatt, S., et al., "Assay of Enzymes of Lipid Metabolism with Colored and Fluorescent Derivatives of Natural Lipids," *Meth. Enzymol.*, 72: 351-375 (1981).

Gill-Randall, R.J., et al., "Is human Type 2 diabetes maternally inherited? Insights from an animal model", *Diabet. Med.* 21(7): 759 (2004).

Hakomori, S. "New Directions in Cancer Therapy Based on Aberrant Expression of Glycosphingolipids: Anti-adhesion and Ortho-Signaling Therapy," *Cancer Cells* 3(12):461-470 (1991).

Hammett, L.P. *Physical Organic Chemistry*, (NY: McGraw), (1940).

Harwood, L.M., et al., "Asymmetric Cycloadditions of Aldehydes to Stabilised Azomethine Ylids: Enantiocontrolled Construction of β-Hydroxy-a-amino acid Derivitives," *Tetrahedron: Asymmetry*, 3(9): 1127-1130 (1992).

Harwood, L.M., et al., "Double diastereocontrol in the synthesis of enantiomerically pure polyoxamic acid," *Chem. Commun.*, 2641-2642 (1998).

Högberg, T., et al., "Theoretical and Experimental Methods in Drug Design Applied on Antipsychotic Dopamine Antagonists." In *Textbook of Drug Design and Development*, pp. 55-91 (1991).

Hospattankar, A.V., et al., "Changes in Liver Lipids After Administration of 2-Decanoylamino-3-Morpholinopropiophenone and Chlorpromazine," *Lipids*, 17(8): 538-543 (1982).

Husain, A., and Ganem, B., "*syn*-Selective additions to Garner aldehyde: synthesis of a potent glucosylceramide synthase inhibitor", *Tetrahedron Letters*, 43: 8621-8623 (2002).

Inokuchi, et al., "Amino Alcohol Esters as Ceramide Analogs and Pharmaceuticals Containing Them for Treatment of Nerve Diseases," Abstract of CAPLUS Accession No. 1998: 786189, JP 10324671 (1998).

Inokuchi, et al., (1996): SNT International HCAPLUS database, Columbus (OH), accession No. 1996: 214749.

Inokuchi, et al., "Aminoalcohol derivatives for treatment of abnormal proliferative diseases", *Chemical Abstracts Service*, XP002495476 retrieved from CAPLUS Database accession No. 1998:816280 (abstract).

Inokuchi, J. et al., "Antitumor Activity via Inhibition of Glycosphingolipid Biosynthesis," *Cancer Lett.*, 38:23-30(1987).

Inokuchi, J., et al., "Preparation of the Active Isomer of 1-phenyl-2-decanoylamino-3-morpholino-1-propanol, Inhibitor of Murine Clucocerebroside Synthetase," *Journal of Lipid Research*, 28: 565-571 (1987).

Inokuchi, J., et al, "Inhibition of Experimental Metastasis of Murine Lewis Lung Carcinoma by an Inhibitor of Glucosylceramide Synthase and Its Possible Mechanism of Action[1]", *Cancer Research*, 50: 6731-6737 (Oct. 15, 1990).

International Preliminary Examination Report for International Application No. PCT/US2002/022659 dated Jul. 24, 2003, titled: "Synthesis of UDP-Glucose: N-Acylsphingosine Glucosyltransferase Inhibitors".

International Preliminary Examination Report on Patentability, issue in International Application PCT/US2000/18935 (WO 01-04108) dated Jul. 20, 2001, titled: "Amino Ceramide-Like Compounds and Therapeutic Methods of Use".

International Preliminary Report on Patentability for International Application No. PCT/US2008/006906, dated Dec. 10, 2009, titled: "2-Acylaminopropoanol-Type Glucosylceramide Synthase Inhibitors".

International Preliminary Report on Patentability for International Application No. PCT/US2002/022659 dated Jul. 24, 2003, titled: "Synthesis of UDP-Glucose: N-Acylsphingosine Glucosyltransferase Inhibitors".

International Preliminary Report on Patentability for International Application No. PCT/US2007/068521 dated Nov. 11, 2008, titled: "Methods of Treating Fatty Liver Disease".

International Preliminary Report on Patentability for International Application No. PCT/US2008/011450 dated Apr. 7, 2010, titled: "Method of Treating Polycystic Kidney Diseases With Ceramide Derivatives".

International Preliminary Report on Patentability for International Application No. PCT/US2009/001773 dated Sep. 21, 2010, titled: "Method of Treating Lupus With Ceramide Derivatives".

International Preliminary Report on Patentability for International Application No. PCT/US2009/051864 dated Feb. 1, 2011, titled: "Glucosylceramide Synthase Inhibition for the Treatment of Collapsing Glomerulopathy and Other Glomerular Diseases".

International Preliminary Report on Patentability, issued in International Application PCT/US2005/040596, dated May 15, 2007, titled: "Methods of Treating Diabetes Mellitus" (14 pages).

International Preliminary Report on Patentability, issued in International Application PCT/US2002/00808, dated Jan. 10, 2003, titled: "Amino Ceramide-Like Compounds and Therapeutic Methods of Use".

International Report on Patentability for International Application PCT/US2007/068521 dated Nov. 11, 2008 with Written Opinion, titled: "Methods of Treating Fatty Liver Disease".

International Search Report for International Application No. PCT/US2000/18935 dated Nov. 28, 2000, titled: "Amino Ceramide-Like Compounds and Therapeutic Methods of Use".

International Search Report for PCT/US2002/00808 dated Oct. 1, 2002, titled: "Amino Ceramide-Like Compounds and Therapeutic Methods of Use".

International Search Report for PCT/US2002/022659 dated Nov. 5, 2002, titled: "Synthesis of UDP-Glucose: N-Acylsphingosine Glucosyltransferase Inhibitors".

Jaffrézou, Jr., et al, "Inhibition of lysosomal acid sphingomyelinase by agents which reverse multidrug resistance," *Biochim. Biophys. Acta*, 1266: 1-8 (1995).

Jankowski, K., "Microdetermination of phosphorus in organic materials from polymer industry by microwave-induced plasma atomic emission spectrometry after microwave digestion", *Microchem. J.*, 70:41-49, 2001.

Jimbo, M., et al., "Development of a New Inhibitor of Glucosylceramide Synthase", *J. Biochem*, 127: 485-491 (2000).

Kabayama, K., et al., "TNFa-induced insulin resistance in adipocytes as a membrane microdomain disorder: involvement in ganglioside GM3", *Glycobiology*, 15(1): 21-29 (2005).

Kalén, A., et al., "Elevated Ceramide Levels in GH4C1 Cells Treated with Retinoic Acid," *Biochimica et Biophysica Acta*, 1125: 90-96 (1992).

Kharkevich, D.A., "Pharmacology", M., Medicament, 47-48 (1987).

Koga, K., and Yamada, S., "Stereochemical Studies. X. Effects of Neighboring Functional Groups on 1,2-Asymmetric Induction in the Reduction of Propiophenone Derivatives with Sodium Borohydride", *Chemical and Pharmaceutical Bulletin*, 20(3): 526-538 (1972).

Kopaczyk, K., C., et al., "In Vivo Conversions of Cerebroside and Ceramide in Rat Brain," *J. Lipid Res.*, 6: 140-145 (1965).

Kurosawa, M., et al., "C-Labeling of novel Atypical β-Adrenoceptor Agonist, SM-11044," *Journal of Labelled Compounds and Radiopharmaceuticals*, 38(3): 285-297 (1996).

Lee, L., et al. "Improved inhibitors of glucosylceramide synthase", *J. Bio Chem.*, 274(21): 14662-14669, 1999.

Levery, S.B., et al., "Disruption of the glucosylceramide biosynthetic pathway in *Aspergillus nidulans* and *Aspergillus fumigatus* by inhibitors of UDP-Glc:ceramide glucosyltransferase strongly affects spore germination, cell cycle, and hyphal growth", *FEBS Letters*, vol. 525, pp. 59-64 (2002).

Masson, E., et al. "a-Series Gangliosides Mediate the Effects of Advanced Glycation End Products on Pericyte and Mesangial Cell

(56) References Cited

OTHER PUBLICATIONS

Proliferation: A Common Mediator for Retinol and Renal Microangiopathy?" *Diabetes*, 54: 220-227 (2005).
Mitchell, S., et al., "Glycosyltransferase Inhibitors: Synthesis of D-*threo*-PDMP, L-*threo*-PDMP, and Other Brain Glucosylceramide Synthase Inhibitors from D- or L-Serine," *J. Org. Chem.*, 63: 8837-8842 (1998).
Miura, T., et al., "Synthesis and Evaluation of Morpholino and Pyrrolidinosphingolipids as Inhibitors of Glucosylceramide Synthase", *Bioorganic and Medicinal Chemistry*, (6) 1481-1489 (1998).
Nakamura, K., et al., "Coomassic Brilliant Blue Staining of Lipids on Thin-Layer Plates," *Anal. Biochem.*, 142: 406-410 (1984).
Natoli, T.A., et al , "Inhibition of glucosylceramide accumulation results in effective blockade of polysystic kidney disease in mouse models" and supplemental information, *Nature Medicine*, 16(7): 788-792 (Jul. 2010).
Nicolaou, K., et al., "A Practical and Enantioselective Synthesis of Glycosphingolipids and Related Compounds. Total Synthesis of Globotriasylceramide (Gb3)," *J. Am. Chem., Soc.*, 110: 7910-7912 (1988).
Nicolaus, B.J.R., "Symbiotic Approach to Drug Design", *Decision Making in Drug Research*, XP-001111439, p. 1-14 (1983).
Nishida, A., et al., "Practical Synthesis of *threo*-(1S, 2S)- and *erythro*-(1R, 2S)-1-Phenyl-2-palmitoylamino-3-morpholino-1-propanol (PPMP) from L-Serine," *Synlett*, 389-390(1998).
Nojiri, H., et al., "Ganglioside GM3: An acidic membrane component that increases during macrophage-like cell differentiation can induce monocytic differentiation of human myeloid and monoctyoid leukemic cell lines HL-60 and U937", *Proc. Natl. Acad. Sci.*, 83: 782-786 (1986).
Notification Concerning Transmittal of International Preliminary Report on Patentability for International Application No. PCT/US2009/005435 dated Apr. 14, 2011, titled: "2-Acylaminopropoanol-Type Glucosylceramide Synthase Inhibitors".
Notification of Transmittal of the International Search Report and Written Opinion of the International Searching Authority from counterpart International Application No. PCT/US2008/006906, dated Dec. 4, 2008, titled: "2-Acylaminopropoanol-Type Glucosylceramide Synthase Inhibitors".
Notification of Transmittal of the International Search Report and the Written Opinion of The International Searching Authority, or the Declaration of International Application No. PCT/US2008/011450, dated Jan. 21, 2009, titled: "Method of Treating Polycystic Kidney Diseases With Ceramide Derivatives".
Notification of Transmittal of the International Search Report and Written Opinion of the International Searching Authority, or the Declaration from counterpart International Application No. PCT/US2009/001773, dated Nov. 11, 2009, titled: "Method of Treating Lupus With Ceramide Derivatives".
Notification of Transmittal of the International Search Report and Written Opinion of the International Searching Authority, or the Declaration from counterpart International Application No. PCT/US2009/051864, dated Nov. 3, 2009, titled: "Glucosylceramide Synthase Inhibition for the Treatment of Collapsing Glomerulopathy and Other Glomerular Diseases".
Notification of Transmittal of the International Search Report and Written Opinion of the International Searching Authority, or the Declaration from counterpart International Application No. PCT/US2009/005435, dated Feb. 12, 2010, titled: "2-Acylaminopropoanol-Type Glucosylceramide Synthase Inhibitors".
Notification of Transmittal of the International Search Report and the Written Opinion of the International Searching Authority, or the Declaration for International Application No. PCT/US2007/068521 dated Nov. 21, 2007, titled: "Methods of Treating Fatty Liver Disease".
Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," *Bioorganic & Medicinal Chemistry Letters*, 7(14): 1915-1920 (1997).
Ong, et al., "Nonalcoholic Fatty Liver Disease and the epidemic of Obesity", *Cleveland Clinic Journal of Medicine*, 71(8): 657-664 (Aug. 2004).
Overkleeft, H.S., et al., "Generation of Specific Deoxynojirimycin-type Inhibitors of the Non-lysosomal Glucosylceramidase," *The Journal of Biological Chemistry*, 273(41):26522-26527 (1998).
Preiss, J., et al., "Quantitative Measurement of sn-1,2-Diacylglycerols Present in Platelets, Hepatocytes, and *ras*-and *sis*-Transformed Normal Rat Kidney Cells," *J. Biol. Chem.*, 261(19): 8597-8600 (1986).
Qian, Q., et al., "Treatment prospects for autosomal-dominant polysystic kidney disease", *Kidney International*, vol. 59, pp. 2005-2002 (2001).
Radin, N.S., "Killing Cancer Cells by Poly-drug elevation of ceramide levels, a hypothesis whose time has come?," *Eur. J. Biochem.* (268(2): 193-204 (2001).
Radin, N.S., et al., "Metabolic Effects of Inhibiting Glucosylceramide Synthesis with PDMP and Other Substances." *Advances in Lipid Research: Sphingolipids, Part B.*, R.M. Bell et al., Eds. (San Diego: Academic Press), 26: 183-213 (1993).
Radin, N.S., et al., "Ultrasonic Baths as Substitutes for Shaking Incubator Baths," *Enzyme*, 45: 567-70(1991).
Radin, N.S., et al., "Use of an Inhibitor of Glucosylceramide Synthesis, $_D$-1-Phenyl-2-decanoylamino-3-morpholino-1-propanol," In *NeuroProtocols: A Companion to Methods in Neurosciences*, S.K. Fisher, et al., Eds., (San Diego: Academic Press) 3: 145-155 (1993).
Rosenwald, A.G., et al., "Effects of a Sphingolipid Synthesis Inhibitor on Membrane Transport Through the Secretory Pathway," *Biochemistry*, 31: 3581-3590 (1992).
Rosenwald, A.G., et al., "Effects of the glucosphingolipid synthesis inhibitor, PDMP, on lysosomes in cultured cells," *J. Lipid Res.*, 35: 1232-1240 (1994).
Rubino, MD., F., et al., "Letter to the Editor", *Annals of Surgery*, 240(2):389-390 (2004).
Sandhoff, K., et al., "Biosynthesis and degradation of mammalian glycosphingolipids" *Phil. Trans. R. Soc. Lond, B* 358 :847-861 (2003).
Sasaki, A., et al., "Overexpression of Plasma Membrane-associated Sialidase Attenuates Insulin Signaling in Transgenic Mice", *The Journal of Biological Chemistry*, 278(30):27896-27902 (2003).
Schwimmer, J.B., et al., "Obesity, Insulin Resistance, and and Other Clinicopathological Correlates of Pediatric Nonalcoholic Fatty Liver Disease", *Journal of Pediatrics*, 143(4): 500-505 (2003).
Shayman, J.A., et al.," Glucosphingolipid Dependence of Hormone-Stimulated Inositol Trisphophate Formation," *J. Biol. Chem.*, 265(21): 12135-12138 (1990).
Shayman, J.A., et al., "Modulation of Renal Epithelial Cell Growth by Glucosylceramide," *The Journal of Biological Chemistry*, 266(34):22968-22974 (1991).
Shukla, A., et al., "Metabolism of D-[$^3$H]*threo*-1-phenyl-2-decanoylamino-3-morpholino-1-propanol, an inhibitor of glucosylceramide synthesis and the synergistic action of an inhibitor of microsomal monooxygenase," *J. of Lipid Research*, 32: 713-722 (1991).
Shukla, G., et al., "Rapid kidney changes resulting from glycosphingolipid depletion by treatment with a glucosyltransferase inhibitor," *Biochimica et Biophysica Acta*, 1083: 101-108 (1991).
Shukla, G.S., et al., "Glucosylceramide Synthase of Mouse Kidney: Further Characterization with an Improved Assay Method[1]," *Arch. Biochem. Biophys.*, 283(2): 372-378 (1990).
Skehan, P., et al., "New Colorimetric Cytotoxicity Assay for Anti-cancer-Drug Screening," *J. Natl. Cancer Inst.*, 82(13): 1107-1112 (1990).
Strum, J.C., et al., "1-β-$_D$-Arabinofuranosylcytosine Stimulates Ceramide and Diglyceride Formation in HL-60-Cells," *J. Biol. Chem.*, 269(22): 15493-15497 (1994).
Svensson, M., et al., "Epithelial Glucosphingolipid Express as a Determinant of Bacterial Adherence and Cytokine Production", *Infection and Immunity*, 62(10): 4404-4410 (1994).

(56) References Cited

OTHER PUBLICATIONS

Tagami, S., et al., "Ganglioside GM3 Participates in the Pathological Conditions of Insulin Resistance", *The Journal of Biological Chemistry*, 227(5): 3085-3092 (2002).

Tang, W., et al., "Phorbol Ester Inhibits 13-Cis-Retinoic Acid-Induced Hydrolysis of Phosphatidylinositol 4,5-Biophosphate in Cultured Murine Keratinocytes: A Possible Negative Feedback via Protein Kinase C-Activation," *Cell Bioch. Funct.*, 9: 183-191 (1991).

Tay-Sachs, URL: http:--www.ninds.nih.gov-disorders-taysachs-taysachs.htm. National Institute of Health of Neurological Disorders and Stroke. Accessed online Sep. 9, 2011.

Uemura, K., et al., "Effect of an Inhibitor of Glucosylceramide Synthesis on Cultured Rabbit Skin Fibroblasts," *J. Biochem.*, (Tokyo) 108(4): 525-530 (1990).

Vunnum, R.,R., et al., "Analogs of Ceramide That Inhibit Glucocerebroside Synthetase in Mouse Brain," *Chemistry and Physics of Lipids*, LD. Bergelson, et al., Eds. (Elsevier-North-Holland Scientific Publishers Ltd.), 26: 265-278 (1980).

Wermuth, C.G., et al.., "Designing Prodrug and Bioprecursors I: Carrier Prodrug", *The Practice of Medicinal Chemistry*, C.G., Wermuth, Ed.(CA: Academic Press Limited), pp. 671-696 (1996).

Wong, C-H., et al., "Synthesis and Evaluation of Homoazasugars as Glycosidase Inhibitors," *J. Org. Chem.*, 60: 1492-1501, (1995).

Yamashita, T., et al., "Enhanced insulin sensitivity in mice lacking ganglioside GM3", *Proc. Natl. Acad. Sci.*, 100(6): 3445-3449 (2003).

Yew, N.S., et al., "Increased Hepatic Insulin Action in Diet-Induced Obese Mice Following Inhibition of Glucosylceramide Synthase" PLoS one, 5(6): 1-9 (Jun. 2010).

Zador, I., et al. "A Role for Glycosphingolipid Accumulation in the Renal Hypertrophy of Streptozotocin-induced Diabetes Mellitus", *J. Clin. Invest.*, 91: 797-803 (1993).

Zhao, H., et al., "Inhibiting Glycosphingolipid Synthesis Ameliorates Hepatic Steatosis in Obese Mice" Hepatology, pp. 85-93 (Jul. 2009)).

Zhao, H., et al., "Inhibiting glycosphingolipid synthesis improves glycemic control and insulin sensitivity in animal models of type 2 diabetes." *Diabetes*, 56(5): 1210-1218 (2007).

Zichc, M. et al., "Angiogenesis Can Be Stimulated or Repressed in Vivo by a Change in GM3 :GD3 Ganglioside Ratio," *Lab. Invest.*, 67:711-715 (1992).

Non-Final Office Action for U.S. Appl. No. 14/532,432, titled: "Method of Treating Polycystic Kidney Diseases With Ceramide Derivatives" Date Mailed: Jan. 5, 2016.

Notice of Allowance and Fee(s) Due for U.S. Appl. No. 14/255,634; titled: "Glucosylceramide Synthase Inhibition for the Treatment of Collapsing Glomerulopathy and Other Glomerular Disease" Date Mailed: Mar. 1, 2016.

Notice of Allowance for U.S. Appl. No. 14/464,432, "Method of Lowering Blood Glucose", dated May 16, 2016.

Cellitti, Susan E., et al., "In vivo incorporation of Unnatural Amino Acids to Probe Structure, Dynamics, and Ligand Binding in a Large Protein by Nuclear Magnetic Resonance Spectroscopy", J. Am. Chem. 130: 9266-9281 (2008).

Gennaro, et al., Remington, The Science and Practice of Pharmacy, Chapter 38, 20th Edition, 2000, pp. 703-712.

Nilsson, O., et al., "The Occurrence of Psychosing and Other Glycolipids in Spleen and Liver From the Three Major Types of Gaucher's Disease", Biochimica et Biophysica Acta, 712 (1982) 453-463.

van Meer, G., et al., "The fate and function of glycosphingolipid glucosylceramide", Phil. Trans. R. Soc. Lond. B (2003) 358, 869-873.

Yatsu, F..M., "Sphingolipidoses", California Medicine, The Western Journal of Medicine, pp. 1-6 (Apr. 1971).

Water / DIO

Formula XI / DIO

Water / Lean

METHODS OF TREATING FATTY LIVER DISEASE

This application is a continuation of U.S. application Ser. No. 12/227,076, filed Dec. 16, 2008, now U.S. Pat. No. 8,716,327, issued May 6, 2014, which is the U.S. National Stage of International Application No. PCT/US2007/068521, filed on May 9, 2007, published in English and claims the benefit of U.S. Provisional Application No. 60/746,811, filed on May 9, 2006, the entire teachings of which are incorporated herein by reference.

FIELD OF THE INVENTION

The invention relates generally to the field of hepatology and inhibition of the synthesis of glucosphingolipids, such as, e.g., the ganglioside GM3, in the liver. More particularly, the invention relates to the use of inhibitors of glucosphingolipid synthesis for the treatment of fatty liver disease and associated conditions. In certain aspects, the invention relates to the use of inhibitors of glucosphingolipid synthesis, such as, e.g., inhibitors of glucosylceramide synthase, lactosylceramide synthase, and/or GM3 synthase, for the treatment of fatty liver disease, including associated conditions.

BACKGROUND OF THE INVENTION

Fatty liver disease (FLD, also know as hepatosteatosis) is a prevalent liver condition that occurs when lipids accumulate in liver cells. The lipid accumulation causes cellular injury and sensitizes the liver to further injuries. The accumulated lipids may also impair hepatic microvascular circulation.

FLD may arise from a number of sources, including excessive alcohol consumption and metabolic disorders, such as those associated with insulin resistance, obesity, and hypertension. Nonalcoholic fatty liver disease (NAFLD) may also result from metabolic disorders such as, e.g., galactosemia, glycogen storage diseases, homocystinuria, and tyrosemia, as well as dietary conditions such as malnutrition, total parenteral nutrition, starvation, and overnutrition. In certain cases, NAFLD is associated with jejunal bypass surgery. Other causes include exposure to certain chemicals such as, e.g., hydrocarbon solvents, and certain medications, such as, e.g., amiodarone, corticosteroids, estrogens (e.g., synthetic estrogens), tamoxifen, maleate, methotrexate, nucleoside analogs, and perhexiline. Acute fatty liver conditions can also arise during pregnancy.

FLD is a prevalent condition. NAFLD alone has been estimated to affect as much as 25-33% of the adult population in the developed world. See, e.g., Cortez-Pinto et al., *J. Am. Med. Assoc.* 282:1659-1664 (1999); Adams et al., *Can. Med. Assoc. J.* 172:899-905 (2005); and Clark et al., *J. Am. Med. Assoc.* 289:3000-3004 (2003). Moreover, NAFLD is also believed to affect as many as 3-10% of obese children.

FLD can progress to more advanced liver disease such as nonalcoholic steatohepatitis (NASH; metabolic steatohepatitis), a condition characterized by liver inflammation and damage, often accompanied by fibrosis or cirrhosis of the liver. NASH may progress to further liver damage ultimately leading to chronic liver failure and, in some cases, hepatocellular carcinoma.

NASH has a prevalence of up to 9% of the general population. See, e.g., Cortez-Pinto et al., *J. Am. Med. Assoc.* 282:1659-1664 (1999). NASH patients have an increased incidence of liver-related mortality. Adams et al., *Can. Med. Assoc. K.* 172:899-905 (2005). About 640,000 adults in the U.S. are estimated to have cirrhosis resulting from NAFLD. Clark et al., *J. Am. Med. Assoc.* 289:3000-3004 (2003). This number may underestimate the actual incidence, as undetected NAFLD is believed to be an important cause of cryptogenic liver cirrhosis. See, e.g., Clark et al., *J. Am. Med. Assoc.* 289:3000-3004 (2003) and Adams et al., *Can. Med. Assoc. J.* 172:899-905 (2005).

There are no treatments for NAFLD whose efficacy has been demonstrated by large-scale rigorous clinical trials. In general, NAFLD patients are advised to exercise, lose weight, and avoid hepatotoxins. Other experimental therapies include antioxidants, cytoprotective agents, antidiabetic agents, insulin-sensitizing agents, and anti-hyperlipidemic agents. See, e.g., Clark et al., *J. Am. Med. Assoc.* 289:3000-3004 (2003) and Adams et al., *Can. Med. Assoc. J.* 172:899-905 (2005).

In view of the high prevalence of disorders associated with hepatic lipid deposits, the severity of these conditions, and the lack of proven treatments, it is important to develop new treatments for such conditions.

SUMMARY

The present invention provides methods of treating FLD in a mammal (such as, e.g., a human) in need of treatment by inhibiting glucosphingolipid synthesis in the mammal. In some embodiments, the mammal is diagnosed with nonalcoholic steatohepatitis, hepatic fibrosis, or hepatic cirrhosis, and/or is at risk for developing fatty liver disease.

Glucosphingolipid (GSL) synthesis may be inhibited by inhibiting the enzymatic activity or expression of one or more GSL enzymes. In general, treatment of the mammal results in a reduction in serum levels of at least one hepatic enzyme (such as, e.g., alanine aminotransferase, aspartate aminotransferase, γ-glutamyltransferase, or alkaline phosphatase) and/or a decrease in hepatic lipid deposits.

The glucosphingolipid whose synthesis is inhibited is chosen from, e.g., glucosylceramide, gangliosides, globo series glucosphingolipids, neolacto series glucosphingolipids, isoglobo series glucosphingolipids, and muco series glucosphingolipids. In certain embodiments, the glucosphingolipid whose synthesis is inhibited is the ganglioside GM3. Inhibition of GM3 can be achieved by inhibition of a GM3 synthesis enzyme chosen from glucosylceramide synthase, lactosylceramide synthase, and GM3 synthase.

In some embodiments, methods of the invention comprise administering to a subject having FLD or at risk for developing FLD a therapeutically effective amount of a composition comprising a glucosylceramide synthase inhibitor of Formula 1:

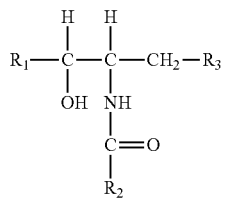

Formula I wherein $R_1$ is chosen from substituted and unsubstituted aryl, substituted and unsubstituted heteroaryl, and substituted or unsubstituted alkyl; $R_2$ is chosen from substituted and unsubstituted alkyl; and $R_3$ is a substituted or unsubstituted tertiary cyclic amino. In some embodiments, $R_3$ is not morpholino when $R_1$ is unsubstituted phenyl and $R_2$ is n-nonyl.

In certain embodiments, $R_1$ is a substituted or unsubstituted phenyl such as, e.g., 1,4-benzodioxan-6-yl. In particular embodiments, $R_2$ comprises at least 1 carbon atom, such as, e.g., $C_1$-$C_2$, $C_1$-$C_6$, $C_2$-$C_{10}$, $C_2$-$C_{20}$, $C_6$-$C_{10}$, $C_{10}$-$C_{14}$, $C_6$-$C_{14}$, $C_6$-$C_9$, and $C_7$-$C_8$ saturated and unsaturated hydrocarbons. In some embodiments, $R_2$ is substituted, e.g., by hydroxyl, alkoxy or aryloxy. For example, in certain embodiments, $R_2$ is $C_2$ alkyl substituted by alkoxy or aryloxy. In some embodiments, $R_2$ comprises at least 7 carbon atoms, such as, e.g., 7, 8, 9, or 10 carbon atoms. In some aspects, $R_2$ is chosen from substituted and unsubstituted $C_7$ alkyl, such as, e.g., 1-(1-hydroxyheptyl) and 1-(6-hydroxyheptyl), and from substituted and unsubstituted $C_8$ alkyl, such as, e.g., 1-(1-hydroxyoctyl) and 1-(7-hydroxyoctyl).

In some embodiments, $R_3$ is pyrrolidino. In more particular embodiments, the compound of Formula I is a 1-(1,4-benzodioxan-6-yl)-2-nonanoylamino-3-pyrrolidino-1-propanol, such as, e.g., 1(R)-(1,4-benzodioxan-6-yl)-2(R)-nonanoylamino-3-pyrrolidino-1-propanol. In other embodiments, the compound of Formula I is a 1-(1,4-benzodioxan-6-yl)-2-octanoylamino-3-pyrrolidino-1-propanol, such as, e.g., 1(R)-(1,4-benzodioxan-6-yl)-2(R)-octanoylamino-3-pyrrolidino-1-propanol.

The foregoing and the following description are exemplary and explanatory only and are not restrictive of the invention, as claimed.

BRIEF DESCRIPTION OF THE FIGURES

In FIG. 1A, large vacuoles are visible throughout the parenchyma of the livers from the water-treated control mice. In FIG. 1B, significantly fewer vacuoles are visible in the livers of mice treated with Formula XI. In FIG. 1C, the livers of normal, lean mice are devoid of any lipid-filled vacuoles.

In FIG. 1A, lower levels of alanine aminotransferase (ALT) are observed in the drug-treated versus placebo-treated control animals. In FIG. 1B, lower levels of aspartate aminotransferase (AST) are observed in the drug-treated versus placebo-treated control animals. In FIG. 1C, lower levels of alkaline phosphatase are observed in the drug-treated versus placebo-treated control animals. In FIG. 1D, lower levels of γ-glutamyltransferase (GGT) are observed in the drug-treated versus placebo-treated control animals.

In FIG. 7A, lower levels of sterol regulatory element binding protein 1c (SREBP-1c) RNA are observed in the drug-treated versus placebo-treated control animals. In FIG. 7B, lower levels of acid citrate lyase 1 (ACL1) are observed in the drug-treated versus placebo-treated control animals. In FIG. 7C, lower levels of acetyl coenzyme A carboxylase 1 (ACC1) are observed in the drug-treated versus placebo-treated control animals. In FIG. 7D, lower levels of fatty acid synthase (FAS) are observed in the drug-treated versus placebo-treated control animals. In FIG. 7E, lower levels of tumor necrosis factor 1 alpha (TNF-α) are observed in the drug-treated versus placebo-treated control animals. In FIG. 7F, lower levels of glucose 6-phosphatase (G6P) are observed in the drug-treated versus placebo-treated control animals. In FIG. 7G, lower levels of procollagen type 1 (collagen) are observed in the drug-treated versus placebo-treated control animals. Thus, treatment with Formula X reduced the expression of genes involved in lipogenesis (SREBP-1c, ACL1, ACC1, FAS), gluconeogenesis (G6P), inflammation (TNF-α), and fibrosis.

DETAILED DESCRIPTION

Figure 1:
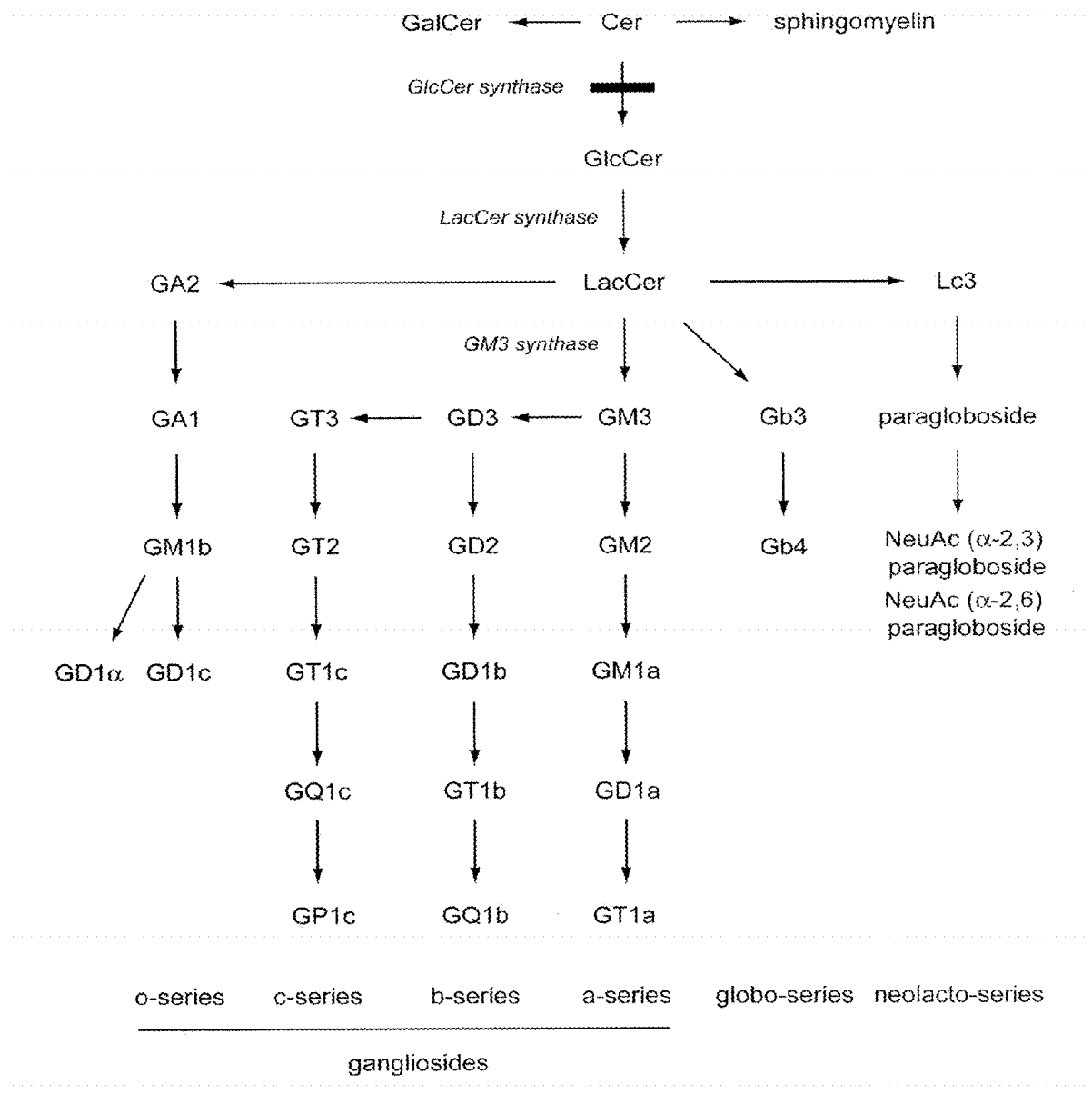
FIG. 1 is a chart of the glycosphingolipid synthesis pathways. In the chart, a wide bar indicates the synthetic step inhibited by inhibitors of glucosylceramide synthase. The following abbreviations are used: Cer, ceramide; GalCer, galactosylceramide; GlcCer, glucosylceramide; LacCer, lactosylceramide. The muco- and isoglobo-synthetic pathways are not depicted.

Glycosphingolipids, glycolipids composed of glycosylated ceramides, are found in plasma membrane, and are involved in a variety of physiological and pathogenic processes, such as cell-cell recognition, immunity, and tumor metastasis. FIG. 1 is a chart depicting the pathways of glycosphingolipid synthesis from ceramide. Glucosphingolipids (GSLs), as used herein, are glucose-containing glycosphingolipids, including GlcCer and glycosphingolipids derived from GlcCer.

GM3, depicted below, is a ganglioside composed of a ceramide molecule glycosylated with a monosialylated trisaccharide. Gangliosides such as GM3 are generally found in microdomains of the outer leaflet of the plasma membrane (Nojiri et al., *Proc. Natl. Acad. Sci. U.S.A.* 83:782-786 (1986)), where they are involved in cell signaling and act as modulators of receptor activity (Yamashita et al., *Proc. Natl. Acad. Sci. U.S.A.* 100:3445-3449 (2003)).

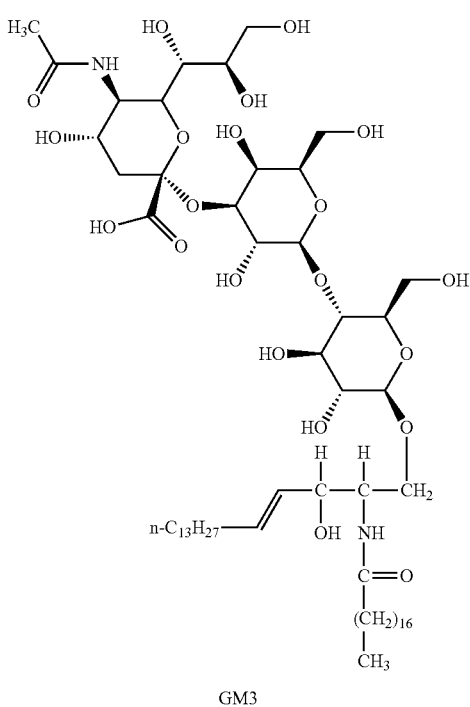

GM3

GM3 is synthesized in the cell by the stepwise enzymatic addition of activated sugar molecules to a ceramide molecule. The first step in the synthesis of GM3 is the addition of glucose to ceramide to form glucosylceramide (GlcCer; glucocerebroside). This step is catalyzed by the enzyme glucosylceramide synthase (UDP-glucose:ceramide glucosyltransferase; ceramide glucosyltransferase; GlcCer synthase; EC 2.4.1.80). In the second step, which is catalyzed by lactosylceramide synthase (UDP-Gal:glucosylceramide β-1,4-galactosyltransferase), a galactose moiety is added to form lactosylceramide. In the third step, a sialic acid (N-acetylneuraminate) is added to the terminal galactose residue of lactosylceramide to form GM3. This step is catalyzed by GM3 synthase (CMP-NeuAc:lactosylceramide α2,3-sialyltransferase; EC 2.4.99.9).

The present invention is based, in part, on the discovery that inhibition of GlcCer synthesis reduces hepatic lipid deposits in a murine model for nonalcoholic fatty liver disease. Accordingly, reduction of downstream GSL (such as, e.g., GM3) levels is expected to be useful in the treatment of FLD. In certain aspects, reduction of GM3 levels, e.g., by inhibition of GlcCer synthase, LacCer synthase, or any of the enzymes involved in the synthesis of GM3, is expected to be useful in the treatment of FLD.

I. Inhibition of Glucosylsphingolipid Synthesis

Methods of inhibiting GSL synthesis include inhibiting the expression and/or enzymatic activity of one or more GSL synthesis enzymes. In some embodiments, the methods include inhibiting the expression and/or enzymatic activity of at least 1, 2, 3, 4, 5, or 6 GSL synthesis enzymes.

A GSL synthesis enzyme is an enzyme that catalyzes any step of the synthesis of the following glucosphingolipids from ceramide: GlcCer, LacCer, GA2, GA1, GM1b, GD1c, GD1α, GM3, GM2, GM1a, GD1a, GT1a, GD3, GD2, GD1b, GT1b, GQ1b, GT3, GT2, GT1c, GQ1c, GP1c, Gb3, Gb4, Lc3, paraglobside, NeuAc (α-2,3) paragloboside, or NeuAc (α-2,6) paragloboside.

A GSL synthesis enzyme may be chosen from, e.g., GlcCer synthase (glucosylceramide synthase), LacCer synthase (lactosylceramide synthase), GA2 synthase, GA1 synthase, GM1b synthase, GD synthase, GD1α synthase, GM3 synthase, GM2 synthase (β-1,4-N-acetylgalactosaminyl-transferase), GM1a synthase, GD1a synthase, GT1a synthase, GD3 synthase, GD2 synthase, GD1b synthase, GT1b synthase, GQ1b synthase, GT3 synthase, GT2 synthase, GT1c synthase, GQ1c synthase, GP1c synthase, Gb3 synthase, Gb4 synthase, Lc3 synthase, paragloboside synthase, NeuAc (α-2,3) paragloboside synthase, and NeuAc (α-2,6) paragloboside synthase. Each of the synthases above is understood to be the enzyme that catalyzes the final step of the synthesis of the respective glucosphingolipid. For example, Gb3 synthase is understood to be the enzyme that catalyzes the final step of the synthesis of Gb3.

The inhibition of a GSL synthesis enzyme's expression may be accomplished at a nucleic acid level, e.g., using antisense nucleic acids and small interfering RNAs (siRNAs). Antisense oligonucleotides are capable of hybridizing to a portion of a coding and/or noncoding region of mRNA by virtue of sequence complementarity, thereby interfering with translation from the mRNA. Antisense nucleic acids may be produced using standard techniques as described in *Antisense Drug Technology: Principles, Strategies, and Applications*, 1st ed., Ed. Crooke, Marcel Dekker (2001). siRNAs are short (e.g., 20-25 nt) double stranded RNAs that inhibit an enzyme of interest via post-transcriptional gene silencing. A specific siRNA may be prepared and used as described in U.S. Pat. No. 6,506,559 and/or using other suitable methods (see, e.g., Appasani (ed.) RNA Interference Technology: From Basic Science to Drug Development, Cambridge University Press, 1st ed., 2005; and Uei-Ti et al. *Nucleic Acids Res.*, 32:936-948 (2004)).

In some embodiments, the inhibition of GSL synthesis is accomplished by administering to the mammal a molecule that inhibits the enzymatic activity (i.e., an inhibitor) of one or more GSL synthesis enzymes. In certain embodiments, a molecule that inhibits the enzymatic activity of a GSL synthesis enzyme may be an analog of the natural substrate of the inhibited GSL synthesis enzyme. Various types of molecules that inhibit enzymatic activity may be obtained by screening appropriate libraries such as, e.g., a small molecule library (Gordon et al., *J. Med. Chem.* 37:1385-1401 (1994); Ecker et al., *BioTechnology* 13:351-360 (1995); Dolle, *J. Comb. Chem.* 2:383-433 (2000)); an oligosaccharide library (York et al., *Carb. Res.* 285:99-128 (1996); Liang et al., *Science* 274:1520-1522 (1996); Ding et al., Adv. Expt. Med. Biol. 376:261-269 (1995); a carbohydrate mimetic library (Byrgesen et al., *Tetrahedron Lett.* 38:5697-5700 (1997)); a glycoprotein or glycolipid library (Karaoglu et al., *J. Cell Biol.* 130:567-577 (1995)); a lipoprotein library (de Kruif et al., *FEBS Lett.* 399:232-236 (1996)); a phage display library of peptides, which can be constrained peptides (see, e.g., U.S. Pat. No. 5,622,699; U.S. Pat. No. 5,206,347; Scott et al., *Science* 249:386-390 (1992); Markland et al., *Gene* 109:13-19 (1991); a peptide library (see, e.g., U.S. Pat. No. 5,264,563; a library of peptide derivative compounds such as a hydroxamate compound library, reverse hydroxamate compound library, a carboxylate compound library, thiol compound library, a phosphinic peptide library or phosphonate compound library (see, e.g., Dive et al., *Biochem. Soc. Trans.* 28:455-460 (2000); Ye et al., *Peptides: The Wave of the Future* (Lebl and Houghten, ed.; American Peptide Society, 2001); a peptidomimetic library (Blondelle et al., *Trends Anal. Chem.* 14:83-92 (1995)); and a nucleic acid library (O'Connell et al., *Proc. Natl. Acad.*

Sci. U.S.A. 93:5883-5887 (1996); Tuerk et al., *Science* 249:505-510 (1990); Gold et al., *Ann. Rev. Biochem.* 64:763-797 (1995).

Inhibitors of GSL synthesis enzymes used in the methods of the invention may be competitive or noncompetitive inhibitors. Competitive inhibitors include substrate analogs (including analogs of a portion of a substrate) which bind to the active site of the enzyme of interest and thereby prevent substrate binding. An inhibitor may inhibit an enzyme with an IC50 of, for example, less than 200, 150, 100, 75, 50, 40, 30, 20, 10, 5, 3, 2, or 1 µM. In certain embodiments, an inhibitor may inhibit an enzyme with an IC50 of less than 1 µM, such as, for example, less than 750, 500, 400, 300, 200, 100 nM. In other embodiments, an inhibitor may inhibit an enzyme with an IC50 of, for example, less than 90, 80, 70, 60, 50, 40, 30, 20, 10, 9, 8, 7, 6, 5, 4, 3, 2, or 1 nM.

Inhibitors of GSL synthesis enzymes used in the methods of the invention include, e.g., tamoxifen, mifepristone, imino sugars (such as, e.g., N-butyldeoxynojirimycin and N-buyldeoxygalactonojirimycin), "P-drugs" (such as, e.g., D,L-threo-1-phenyl-2-decanoylamino-3-morpholino-1-propanol (PDMP) and analogs thereof, (R,R)-(D-threo)1-phenyl-2-decanoylamino-3-morpholino-1-propanol, D-threo-4'-hydroxy-1-phenyl-2-palmitoylamino-2-pyrrolidino-1-propanol, D-threo-4'-hydroxy-1-phenyl-2-palmitoylamino-2-pyrrolidino-1-propanol, D,L-threo-1-phenyl-2-hexadecanoylamino-3-morpholino-1-propanol, and D-threo-1-(3',4'-ethylenedioxy)phenyl-2-palmitoylamino-3-pyrrolidine-1-propanol, and anti-androgens, which are inhibitors of glucosylceramide synthesis include. In certain embodiments, the inhibitor of glucosylceramide synthase is not PDMP. Inhibitors of GSL synthesis enzymes further include inhibitors of GM1 synthesis such as, e.g., tunicamycin. Inhibitors of GSL synthesis enzymes further include inhibitors of GM2 synthesis such as, e.g., tunicamycin. Yusuf et al., *Proc. Natl. Acad. Sci. U.S.A.* 80:7075-7079 (1983) Inhibitors of GSL synthesis enzymes also include inhibitors of GM3 synthesis including, e.g., antisense-type inhibitors (see, e.g., Deng et al., *Glycobiology* 12:145-152 (2002)). Inhibitors of GSL synthesis enzymes further include sialyltransferase inhibitors such as, e.g., lithocholic acid analogues (see, e.g., Chang et al., *Chem. Commun.* 629-631 (2006)).

In certain embodiments, the methods cause a decrease in the synthesis of at least one glucosphingolipid chosen from glucosylceramide, a ganglioside (such as, e.g., an a-series ganglioside, a b-series ganglioside, a c-series ganglioside, and an o-series ganglioside), a globo-series glucosphingolipid, a neolacto-series glucosphingolipid, an isoglobo-series glucosphingolipid, and a muco-series glucosphingolipid. For example, in some embodiments, the methods cause a decrease in the synthesis of an a-series ganglioside, such as, e.g., the ganglioside GM3.

II. Inhibition of GM3 Synthesis

In certain embodiments, inhibition of GSL synthesis comprises inhibition of GM3 synthesis. Methods of inhibiting GM3 synthesis include inhibiting the expression and/or enzymatic activity of one or more GM3 synthesis enzymes, which include (a) glucosylceramide synthase, (b) lactosylceramide synthase, and (c) GM3 synthase.

Exemplary Inhibitors of Glucosylceramide Synthase

Inhibitors of glucosylceramide synthase include, e.g., substrate analogs which bind to the enzyme active site and prevent substrate binding. These inhibitors include ceramide analogs, as described in, e.g., U.S. Pat. Nos. 6,569,889; 6,255,336; 5,916,911; 5,302,609; Lee et al., *J. Biol. Chem.* 274:14662-14669 (1999)) and sugar analogs, as described in, e.g., U.S. Pat. Nos. 6,660,749; 6,610,703; 5,472,969; 5,525,616; and Overkleef et al., *J. Biol. Chem.* 273(41): 26522-26527 (1998).

In specific embodiments, the inhibitors may be analogs of a substrate or a portion of a substrate of glucosylceramide synthase, such as e.g., a ceramide analog or glucosylceramide analog. Suitable ceramide analogs include those described in U.S. Pat. Nos. 6,569,889; 6,255,366; 6,051,598, 5,916,911; Inokuchi et al., *J. Lipid Res.* 28:565 (1987); Shayman et al., *J. Biol. Chem.* 266:22968 (1991); and Bell et al., Ed., 1993, *Advances in Lipid Research: Sphingolipids in Signaling* (Academic Press, San Diego).

In some embodiments, the invention provides an inhibitor of glucosylceramide synthase that is a 2-amino-1-propanol ceramide analog of Formula I:

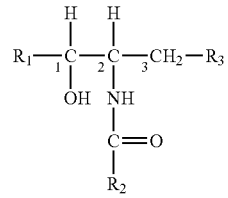

Formula I wherein $R_1$, $R_2$, and $R_3$ are set forth below. Such inhibitors may be prepared as described in, e.g., U.S. Pat. No. 6,855,830.

In certain embodiments, $R_1$ is chosen from substituted or unsubstituted aryl and substituted or unsubstituted heteroaryl. In certain aspects, one or more hydrogen atoms of $R_1$ may be replaced by a suitable substituent such as, e.g., acyl, acylamino, acyloxy, alkenyl, alkoxy, alkyl, alkynyl, amido, amino (e.g., substituted or unsubstituted amino), aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. In certain embodiments, one or more methylene groups of a substituent may be substituted by a heteroatom such as, e.g., oxygen, nitrogen, or sulfur.

For example, $R_1$ may be substituted phenyl, such as, e.g., phenyl substituted with hydroxy, alkoxy (such as, e.g., $C_1$-$C_{20}$, $C_{10}$-$C_{20}$, $C_3$-$C_{15}$, or $C_7$-$C_{12}$ alkoxy, including, e.g, ethoxy and methoxy), or halo (e.g., iodo, bromo, chloro, or fluoro). In particular embodiments, $R_1$ is chosen from 2-hydroxyphenyl, 3-hydroxyphenyl, 4-hydroxyphenyl, 2-methoxyphenyl, 3-methoxyphenyl, 4-methoxyphenyl, 3,4-dimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, or 4-iodophenyl. In other embodiments, $R_1$ is chosen from 2-(trifluoromethyl)phenyl, 3-(trifluoromethyl)phenyl, 4-(trifluoromethyl)phenyl, 2-(trifluoromethoxy)phenyl, and 3-(trifluoromethoxy)phenyl, 4-(trifluoromethoxy)phenyl.

In certain aspects, $R_1$ is chosen from phenyl fused with at least one aryl, cycloalkyl, or heterocyclyl ring. For example, $R_1$ may be a phenyl ring fused with a 1,4-dioxane ring, i.e., 3,4-ethylenedioxyphenyl or 1,4-benzodioxanyl (Formula II). In particular embodiments, $R_1$ may be 1,4-benzodioxan-6-yl (Formula IIa) or 1,4-benzodioxan-5-yl (Formula IIb).

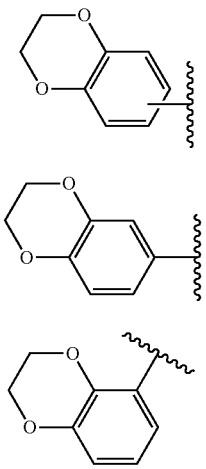

Formula II

Formula IIa

Formula IIb

In other embodiments, $R_1$ may be, e.g., 3,4-methylenedioxyphenyl (1,3-benzodioxolyl; Formula III) or 3,4-propylenedioxyphenyl (Formula IV).

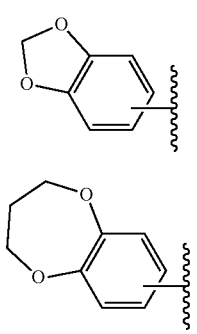

Formula III

Formula IV

In some embodiments, $R_1$ is chosen from substituted or unsubstituted straight and branched alkyl, alkenyl, and alkynyl (saturated and unsaturated hydrocarbons). The saturated or unsaturated hydrocarbon may be, chosen from, e.g., $C_2$-$C_{20}$, $C_2$-$C_{12}$, $C_2$-$C_6$, $C_3$-$C_{15}$, and $C_7$-$C_{12}$ saturated and unsaturated hydrocarbons. In certain embodiments, $R_1$ is chosen from alkenyl groups such as, e.g., alk-1-en-1-yl groups. In certain embodiments, the 1-propanol group is an allylic alcohol. For example, the compound of Formula I is an allylic alcohol in embodiments wherein $R_1$ is, e.g., 1-pentenyl, 1-hexenyl, 1-heptenyl, 1-octenyl, 1-nonenyl, 1-decenyl, 1-undecenyl, or 1-dodecenyl.

The saturated or unsaturated hydrocarbon may be substituted by a suitable substituent such as, e.g., acyl, acylamino, acyloxy, alkenyl, alkoxy, alkyl, alkynyl, amido, amino (e.g., substituted or unsubstituted amino), aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. In certain embodiments, one or more methylene groups of the saturated or unsaturated hydrocarbon, or of a substituent thereof, may be substituted by a heteroatom such as, e.g., oxygen, nitrogen, or sulfur. In certain embodiments, the saturated or unsaturated hydrocarbon may be substituted with at least one hydroxyl group. For example, the saturated or unsaturated hydrocarbon may be substituted with a hydroxyl group positioned 1, 2, 3, 4, or 5 carbon atoms away from carbon 1 or carbon 2 of Formula I.

In certain embodiments, $R_2$ is chosen from substituted or unsubstituted saturated and unsaturated hydrocarbons such as, e.g., $C_1$-$C_2$, $C_1$-$C_4$, $C_1$-$C_6$, $C_2$-$C_{10}$, $C_1$-$C_{20}$, $C_6$-$C_{10}$, $C_{10}$-$C_{14}$, $C_6$-$C_{14}$, $C_6$-$C_9$, and $C_7$-$C_8$ saturated and unsaturated hydrocarbons. In other embodiments, $R_2$ is chosen from substituted or unsubstituted $C_5$, $C_6$, $C_7$, $C_8$, and $C_9$ saturated and unsaturated hydrocarbons. In certain embodiments, $R_2$ is chosen from saturated and unsaturated hydrocarbons substituted with at least one substituent chosen from acyl, acylamino, acyloxy, alkenyl, alkoxy, alkyl, alkynyl, amido, amino (e.g., substituted or unsubstituted amino), aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. In certain embodiments, one or more methylene groups of $R_2$, or of a substituent thereof, may be substituted by a heteroatom such as, e.g., oxygen, nitrogen, or sulfur. For example, $R_2$ may be a saturated or unsaturated hydrocarbon substituted with at least one hydroxyl, alkoxy, or aryloxy group, such as a $C_1$-$C_2$, $C_1$-$C_4$, $C_1$-$C_6$, $C_2$-$C_{10}$, $C_1$-$C_{20}$, $C_6$-$C_{10}$, $C_{10}$-$C_{14}$, $C_6$-$C_{14}$, $C_6$-$C_9$, and $C_7$-$C_8$ saturated or unsaturated hydrocarbon substituted with at least one hydroxyl, alkoxy, or aryloxy group, where the alkoxy or aryloxy group may be substituted. For example, the alkoxy or aryloxy group may be substituted by at least one substituent chosen from acyl, acylamino, acyloxy, alkenyl, alkoxy, alkyl, alkynyl, amido, amino (e.g., substituted or unsubstituted amino), aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido.

In embodiments wherein $R_2$ is 1-heptyl, the 1-heptyl may be substituted at, e.g., position 1 and/or 6, and in embodiments wherein $R_2$ is 1-octyl, the 1-octyl may be substituted at, e.g., position 1 and/or 7. For example, $R_2$ may be 1-(1-hydroxyheptyl) (Formula V), 1-(6-hydroxyheptyl) (Formula VI), 1-(1-hydroxyoctyl) (Formula VII), or 1-(7-hydroxyoctyl) (Formula VIII).

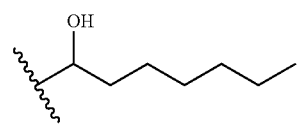

Formula V

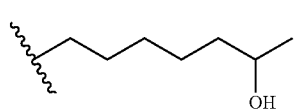

Formula VI

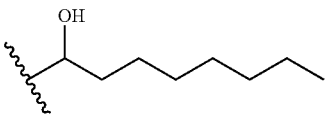

Formula VII

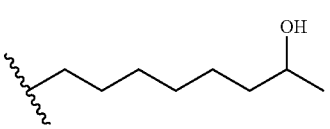

Formula VIII

In some embodiments, $R_2$ is $C_2$-$C_{10}$ alkyl substituted by optionally substituted alkoxy or aryloxy. For example, in some embodiments $R_2$ is $C_2$-$C_4$ alkyl substituted by optionally substituted alkoxy or aryloxy. In particular embodiments, $R_2$ is $C_2$ alkyl substituted by aryloxy such as 4-methoxyphenoxy.

In certain embodiments, $R_3$ is substituted or unsubstituted amino such as, e.g., secondary or tertiary amino. In some embodiments $R_3$ has the structure of Formula IX below, where a wavy line indicates the point of attachment of the amino group.

Formula IX $R_{18}$ and $R_{19}$ may each be independently selected from, e.g., hydrogen, acyl, acyloxy, alkenyl, alkoxy, alkyl, alkynyl, aryl, aryloxy, carbamoyl, carboalkoxy, carboxy, cycloalkyl, formyl, heteroaryl, heterocyclyl, hydroxy, imino, nitro, oxo, sulfinyl, sulfonyl, and thio. In certain embodiments, $R_{18}$ and $R_{19}$ may be substituted with at least one substituent chosen from acylamino, acyloxy, alkenyl, alkoxy, alkyl, alkynyl, amido, amino, aryl, aryloxy, azido, carbamoyl, carboalkoxy, carboxy, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonate, sulfonyl, thio, thioacylamino, thioureido, and ureido. In certain embodiments, one or more methylene groups of $R_{18}$, $R_{19}$, or a substituent thereof, may be substituted by a heteroatom such as, e.g., oxygen, nitrogen, or sulfur.

In other embodiments, $R_3$ has the structure of Formula IX, where $R_{18}$ and $R_{19}$ are taken together with N to form a heterocyclyl (i.e., $R_3$ is a tertiary cyclic amino). The heterocyclyl may be substituted or unsubstituted by, e.g., at least one substituent independently selected from acyl, alkyl, alkenyl, alkenoxy, alkynyl, aldehyde, alkoxy, amido, amino, aryl, aryloxy, carboxy, cyano, cycloalkyl, ether, ester, halogen, heteroaryl, heterocyclyl, hydroxy, keto, nitro, oxo, perfluoroalkyl, sulfonyl, sulfonate, and thio. In certain embodiments, one or more methylene groups of the heterocyclyl, or a substituent thereof, may be substituted by a heteroatom such as, e.g., oxygen, nitrogen, or sulfur.

In some embodiments, the heterocyclyl is, e.g., pyrrolidino, azetidino, piperidino, piperazino, morpholino, thiomorpholino, or hexamethyleneimino. In particular embodiments, the heterocyclyl is not morpholino. For example, in certain embodiments, $R_3$ is not morpholino when $R_1$ is unsubstituted phenyl and $R_2$ is n-nonyl. In certain embodiments, $R_3$ is not morpholino, irrespective of all other groups.

In a specific embodiment the glucosylceramide synthase inhibitor is 1-(1,4-benzodioxan-6-yl)-2-nonanoylamino-3-pyrrolidino-1-propanol (Formula X), or a salt thereof.

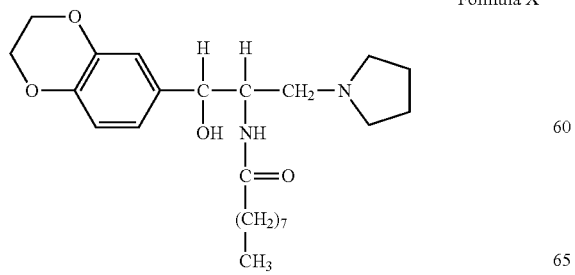

Formula X

For example, the glucosylceramide synthase inhibitor may be 1(R)-(1,4-benzodioxan-6-yl)-2(R)-nonanoylamino-3-pyrrolidino-1-propanol, 1(R)-(1,4-benzodioxan-6-yl)-2(S)-nonanoylamino-3-pyrrolidino-1-propanol, 1(S)-(1,4-benzodioxan-6-yl)-2(R)-nonanoylamino-3-pyrrolidino-1-propanol, or 1(S)-(1,4-benzodioxan-6-yl)-2(S)-nonanoylamino-3-pyrrolidino-1-propanol. In particular embodiments, the glucosylceramide synthase inhibitor is 1(R)-(1,4-benzodioxan-6-yl)-2(R)-nonanoylamino-3-pyrrolidino-1-propanol (i.e., D-threo-1-(1,4-benzodioxan-6-yl)-2(R)-nonanoylamino-3-pyrrolidino-1-propanol).

In another embodiment the glucosylceramide synthase inhibitor is 1-(1,4-benzodioxan-6-yl)-2-octanoylamino-3-pyrrolidino-1-propanol (Formula XI), or a salt thereof.

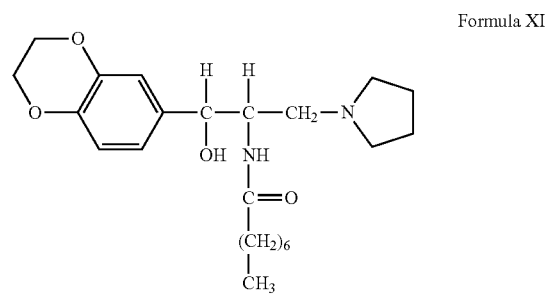

Formula XI

For example, the glucosylceramide synthase inhibitor may be 1(R)-(1,4-benzodioxan-6-yl)-2(R)-octanoylamino-3-pyrrolidino-1-propanol, 1(R)-(1,4-benzodioxan-6-yl)-2(S)-octanoylamino-3-pyrrolidino-1-propanol, 1(S)-(1,4-benzodioxan-6-yl)-2(R)-octanoylamino-3-pyrrolidino-1-propanol, or 1(S)-(1,4-benzodioxan-6-yl)-2(S)-octanoylamino-3-pyrrolidino-1-propanol. In particular embodiments, the glucosylceramide synthase inhibitor is 1(R)-(1,4-benzodioxan-6-yl)-2(R)-octanoylamino-3-pyrrolidino-1-propanol (i.e., D-threo-1-(1,4-benzodioxan-6-yl)-2-octanoylamino-3-pyrrolidino-1-propanol).

In another embodiment the glucosylceramide synthase inhibitor is 1-(1,4-benzodioxan-6-yl)-2-(4-methoxyphenoxy)propanoylamino-3-pyrrolidino-1-propanol (Formula XII), or a salt thereof.

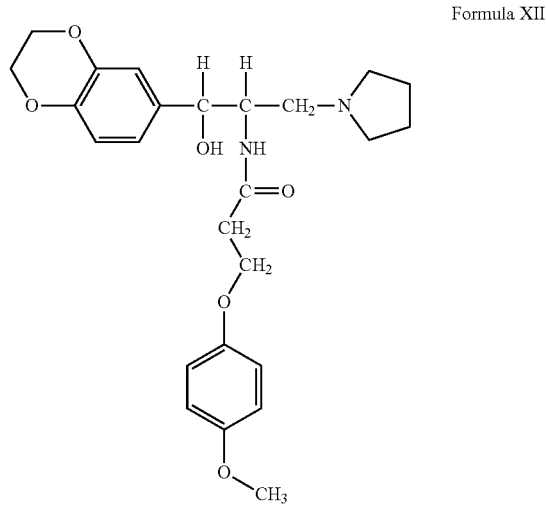 [SMILES: COc1ccc(OCCC(=O)NC(CN2CCCC2)C(O)c2ccc3c(c2)OCCO3)cc1]

Formula XII

For example, the glucosylceramide synthase inhibitor may be 1(R)-(1,4-benzodioxan-6-yl)-2(R)-(4-methoxyphenoxy)propanoylamino-3-pyrrolidino-1-propanol, 1(R)-(1,4-benzodioxan-6-yl)-2(S)-(4-methoxyphenoxy)propanoylamino-3-pyrrolidino-1-propanol, 1(S)-(1,4-benzodioxan-6-yl)-2(R)-(4-methoxyphenoxy)propanoylamino-3-pyrrolidino-1-propanol, or 1(S)-(1,4-benzodioxan-6-yl)-2(S)-(4-methoxyphenoxy)propanoylamino-3-pyrrolidino-1-propanol. In particular embodiments, the glucosylceramide synthase inhibitor is 1(R)-(1,4-benzodioxan-6-yl)-2(R)-(4-methoxyphenoxy)propanoylamino-3-pyrrolidino-1-propanol (i.e., D-threo-1-(1,4-benzodioxan-6-yl)-2(R)-(4-methoxyphenoxy)propanoylamino-3-pyrrolidino-1-propanol).

Methods of making the glucosylceramide synthase inhibitors set forth above have been described in, e.g., U.S. Pat. Nos. 6,569,889; 6,255,336; 5,916,911; 5,302,609; Lee et al., *J. Biol. Chem.* 274:14662-14669 (1999); Abe et al., *J. Biochem.* 111:191-196 (1992); Inokuchi et al., *J. Lipid Res.* 28:565-571 (1987).

In certain embodiments, the compounds of Formula I specifically inhibit glucosylceramide synthase relative to another GSL synthesis enzyme. For example, a compound of Formula I may inhibit glucosylceramide synthase at least, e.g., 2, 3, 4, 5, 10, 15, 20, 100, or 1000-fold more effectively than GM3 synthase or lactosylceramide synthase. In other embodiments, the compounds of Formula I may inhibit at least one other GSL synthesis enzyme.

The compounds of Formula I may be tested for the ability to inhibit glucosylceramide synthase. Assays for glucosylceramide synthase activity are described in, e.g., U.S. Patent Appl. No. 2004/0097551 A1; Platt et al., *J. Biol. Chem.* 269:27108-27114 (1994); Gouazé et al., *Mol. Cancer Ther.* 3:633-640 (2004); Chujor et al., *J. Lipid Res.* 39:277-285 (1998); Shayman et al., *Meth. Enzymol.* 311:42-9 (2000); and Hayashi et al., *Anal. Biochem.* 345:181-186 (2005).

Exemplary Inhibitors of Lactosylceramide Synthase

Inhibitors of lactosylceramide synthase include, e.g., antisense oligonucleotides, siRNAs, and inhibitory molecules chosen from, e.g., small molecules, oligosaccharides, carbohydrate mimetics, glycoproteins, glycolipids, lipoproteins, peptides, peptide derivatives, peptidomimetics, and nucleic acids. In some embodiments, the inhibitor of lactosylceramide synthase is gluco-4-epoxy-4-C-methylenegly-cosyceramide (see, e.g., Zacharias et al., *J. Biol. Chem.* 269:13313-13317 (1994)).

Inhibition of lactosylceramide activity may assessed by any suitable assay, such as, e.g., the assay described in Hayashi et al., *Anal. Biochem.* 345:181-186 (2005).

Exemplary Inhibitors of Inhibitors of GM3 Synthase

Inhibitors of GM3 synthase include, e.g., antisense oligonucleotides, siRNAs, and inhibitory molecules chosen from, e.g., small molecules, oligosaccharides, carbohydrate mimetics, glycoproteins, glycolipids, lipoproteins, peptides, peptide derivatives, peptidomimetics, and nucleic acids.

Particular inhibitors of GM3 synthase include, e.g., those described in International Patent Appl. Pub. No. WO 2005/108600. In some embodiments, the inhibitor of GM3 synthase is a carbon-linked analog of cytidine monophospho-N-acetylneuraminic acid (CMP-NANA), as described in Hatanaka et al., *Heterocycles* 43:531-534 (1996).

Inhibition of GM3 synthase activity may assessed by any suitable assay, such as, e.g., the assays described in International Patent Appl. Pub. No. WO 2005/108600, International Patent Appl. Pub. No. WO 97/47749, U.S. Pat. No. 6,555,371, Wakarchuk et al., *J. Biol. Chem.* 271:19166-19173 (1996); Hatanaka et al., *Chem. Pharm. Bull.* 44:1111-1115 (1996); and Preuss et al., *J. Biol. Chem.* 268:26273-26278 (1993).

III. Methods of Treatment

The invention provides methods of treating FLD by inhibition of GSL synthesis. In certain embodiments, the invention provides methods of treating FLD by inhibition of GSL synthesis. In some embodiments, inhibition of GSL synthesis may be inhibition of GM3 synthesis. These methods may include (a) identifying a mammal in need of the treatment and (b) administering to the mammal a composition that inhibits GSL synthesis, thereby treating FLD.

The term "treat" and its cognates refer to delaying the onset, slowing the progression, or reducing the severity of a disease and associated conditions or symptoms and does not require a complete cure of a disease.

The term "fatty liver disease" (FLD) refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

A mammal in need of treatment may be one who is at increased risk of developing FLD. For example, a subject having abnormal fat metabolism, alcoholism, advanced age (e.g., greater than 40, 50, 60, or 70 years of age), celiac disease, diabetes mellitus (e.g., type II diabetes mellitus), dyslipidemia, exposure to industrial solvents, galactosemia, glycogen storage diseases, homocystinuria, hyperferritinemia, hyperinsulinemia, hyperlipidemia, hypertension, hypertriglyceridemia (e.g. ≥1.7 mmol/L or ≥151 mg/dL), hyperuricemia, hypoxia, impaired fasting glycemia, inborn metabolic disorders (e.g., related to galactose, glycogen, homocysteine, or tyrosine metabolism), insulin resistance, iron overload, jejunal bypass surgery, low levels of high-density lipoprotein, Madelung's lipomatosis, malnutrition, Mauriac syndrome, metabolic syndrome, mitochondrial dysfunction, mitochondrial injury, mitochondrialopathies, niacin deficiency, Niemann-Pick disease, obesity (especially visceral adiposity or central obesity), overnutrition, pantothenic acid deficiency, peroxisomal diseases, polycystic ovarian syndrome, pregnancy, rapid weight loss, riboflavin deficiency, sleep apnea, starvation, tyrosemia, Weber-Christian disease, or Wilson's disease may have, or be at increased risk of developing, a disorder associated with hepatic lipid deposits. NAFLD has also been associated with rapid weight loss. In addition, patients treated with certain medications, such as, e.g., amiodarone, corticosteroids, estrogens (e.g., synthetic estrogens), maleate, methotrexate, perhexyline, salicylate, tamoxifen, tetracycline, and valproic acid may have, or be at increased risk of developing, a disorder associated with hepatic lipid deposits.

A subject in need of treatment may be presumptively diagnosed on the basis of symptoms. However, steatosis, particularly macrovesicular steatosis (in which hepatocytes are filled with large lipid droplets which displace the nuclei to the periphery), is often asymptomatic in adults and children. Alcohol-related fatty liver disease in general, is often asymptomatic. Microvesicular steatosis (in which hepatocytes are filled with small lipid droplets, and nuclei are centrally located) is more commonly symptomatic. NAFLD may also be more likely to be symptomatic in children. Carey et al., eds., 1998, *The Washington Manual of Medical Therapeutics*, 29th ed. (Lippincott Williams & Williams, Philadelphia).

Symptoms of a disorder associated with hepatic lipid deposits, when present, may be valuable in establishing a presumptive diagnosis. Such symptoms include, e.g., abdominal discomfort (e.g., discomfort in the right upper abdominal quadrant), acanthosis nigricans, bowel dismotility, coma, constipation, disseminated intravascular coagulopathy, epigastric pain, fatigue, hepatomegaly (generally with a smooth, firm surface upon palpation), hypoglycemia, jaundice, lipomatosis, lipoatrophy, lipodystrophy, nausea, neurological defects, Palmer erythema, panniculitis, periumbilical pain, small bowel bacterial overgrowth, spider angiomata, splenomegaly, subacute liver failure, and vomiting.

A subject in need of treatment may also be presumptively diagnosed by serum tests of liver enzymes. For example, steatosis may be indicated by elevated serum levels (often moderately elevated, e.g., elevated approximately 2, 3, 4, 5, 6, 7, 9, 10, 11, or 12-fold above normal levels) of liver enzymes (such as, e.g., alanine aminotransferase, aspartate aminotransferase, γ-glutamyltransferase, alkaline phosphatase) when other causes (such as, e.g., acute hepatitis, autoimmune disease, chronic hepatitis, cirrhosis, fulminant hepatitis, hepatocellular carcinoma, metastatic carcinoma, right heart failure, and viral hepatitis) have been eliminated. For example, alanine aminotransferase (ALT or SGPT) values greater than 32, 24, or 56 units per liter of serum or at least 2, 3, 4, 5, 6, 7, 8, 9, 10, 11, 12, or more times normal values may be indicative of a disorder associated with hepatic lipid deposits, or by aspartate aminotransferase (AST or SGOT) values greater than 40 units per liter of serum or at least 2, 3, 4, 5, 6, 7, 8, 9, 10, 11, 12, or more times normal values. The ratio of AST to ALT is often less than one in NAFLD, but may be greater than one in patients with alcoholic liver disease or advanced liver disease. In addition, γ-glutamyltransferase levels may be significantly elevated, e.g., at least 2, 3, 4, 5, 6, 7, 8, 9, 10, 11, 12, or more times normal values. The mean corpuscular volume (MPV) may be greater than, e.g., 86, 98, 100, or 110 femtoliters.

A subject in need of treatment may also be presumptively diagnosed by noninvasive imaging techniques (e.g., ultrasonography, computed tomography, and magnetic resonance imaging) when steatosis is greater than, e.g., 25% or 30%. In general, it may be difficult to distinguish between NAFLD and NASH to detect fibrosis, or to determine the progression of disease, by such imaging methods. NAFLD may present as a focal or diffuse accumulation of lipid, but in NASH the lipid is generally diffuse. NAFLD may also be detected by magnetic resonance spectroscopy, a technique which may be of value for quantitative determination of hepatic lipid levels. For example, determination of hepatic triglyceride levels by MRI has been demonstrated to correlate with histologic biopsy results. See, e.g., Kawamitsu et al., *Magn. Reson. Med. Sci.* 2:47-50 (2003).

A subject in need of treatment may be definitively diagnosed by liver biopsy. A liver is considered to be steatotic when a biopsy reveals at least 5-10% w/w fatty deposits (in practice, this is value may be determined microscopically as the fraction of lipid-filled hepatocytes). See, e.g., Clark et al., *J. Am. Med. Assoc.* 289:3000-3004 (2003) and Adams et al., *Can. Med. Assoc. J.* 172:899-905 (2005). A liver with fatty deposits comprising up to 25% w/w may be considered mildly steatotic, and a liver with fatty deposits comprising greater than 25% w/w may be considered severely steatotic. Histological findings indicative of NASH include steatosis, hepatocyte ballooning, lobular inflammation, Mallory hyaline bodies, mixed inflammatory infiltrate, pericellular fibrosis, and perisinusoidal fibrosis. Additional information may be found in, e.g., Neuschwander-Tetri et al., *Hepatology* 37:1202-1219 (2003).

Disease progression in NAFLD/NASH, as assessed by fibrosis in liver histology, has been reported to correlate with the degree of insulin resistance and other features of metabolic syndrome. Ryan et al., *Diabetes Care,* 28:1222-1224 (2005). Elevated levels of serum immunoglobulin A have also been associated with disease progression. Neuschwander-Tetri et al., *Hepatology* 37:1202-1219. Other markers proposed to be related to fibrosis in NAFLD patients include laminin, hyaluronan, type IV collagen, and aspartate aminotransferase. DosSantos et al., *Braz. J. Med. Biol. Res.* 38:747-753 (2005). Female gender is also associated with more rapid disease progression.

Efficacy of treatment may also be determined by detection of a reduction in one or more symptoms or clinical manifestations of a disease as well as any of the test described above for diagnosis.

Administration of an inhibitor of a GSL synthesis enzyme, such as, e.g., a compound of Formula I, to a subject may reduce serum levels of a hepatic enzyme (e.g., alanine aminotransferase, aspartate aminotransferase, γ-glutamyltransferase, or alkaline phosphatase) at least 10%, such as, e.g., at least 15, 20, 30, 40, 50, 60, 62, 64, 66, 68, or 70%, as compared to pre-treatment control.

Administration of an inhibitor of a GSL synthesis enzyme, such as, e.g., a compound of Formula I, to a subject may reduce serum levels of a disease marker (such as, e.g., laminin, hyaluronan, type IV collagen, or immunoglobulin A) at least 10%, such as, e.g., at least 15, 20, 30, 40, 50, 60, 62, 64, 66, 68, or 70%, as compared to pre-treatment control. Administration of an inhibitor of a GSL synthesis enzyme, such as, e.g., a compound of Formula I, to a subject may reduce, e.g., hyperlipidemia, hypertriglyceridemia, or insulin resistance at least 10%, such as, e.g., at least 15, 20, 30, 40, 50, 60, 62, 64, 66, 68, or 70%.

Administration of an inhibitor of a GSL synthesis enzyme, such as, e.g., a compound of Formula I, to a subject may reduce histological features of a hepatic disorder associated with lipid deposition such as, e.g., cholestasis, fat cysts, fibrosis, granular iron, hepatocellular ballooning, increased numbers of eosinophils, inflammation, lobular disarray, lobular inflammation, macrovesicular steatosis, Mallory bodies, megamitochondria, necrosis, periodic acid-Schiff stained globules, portal inflammation, microvesicular steatosis, or steatosis, as determined by sequential liver biopsies. For example, the fraction of hepatocytes having pathogenic lipid deposits and/or the over-all amount of liver fat (e.g., triglycerides) may be reduced by, e.g., at least 15, 20, 30, 40, 50, 60, 62, 64, 66, 68, or 70%, as compared to pre-treatment control.

IV. Pharmaceutical Compositions, Modes of Administration and Dosing

Pharmaceutical compositions for use in the methods of the invention are provided. The compositions of the invention comprise an inhibitor of GSL synthesis, which may, in certain embodiments, be an inhibitor of GM3 synthesis (such as, e.g., a compound of Formula I) and a pharmaceutically acceptable carrier (excipient). Examples of suitable pharmaceutical carriers are described in, e.g., Martin, 1990, *Remington's Pharmaceutical Sciences,* 17th ed. (Mack Pub. Co., Easton, Pa.). Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The compositions of the invention may also contain pH buffering reagents and wetting or emulsifying agents. The compositions may further contain other active compounds providing supplemental, additional, or enhanced therapeutic functions. The pharmaceutical compositions may also be included in a container, pack, or dispenser together with instructions for administration.

Suitable pharmaceutically acceptable salts of the compounds of the invention may also be included in the pharmaceutical compositions. Examples of salts include salts of inorganic acids (such as, e.g., hydrochloric, hydrobromic, phosphoric, metaphosphoric, nitric, and sulfuric acids) and of organic acids (such as, e.g., acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Other suitable pharmaceutically acceptable basic salts include ammonium salts, alkali metal salts (such as, e.g., sodium and potassium salts) and alkaline earth metal salts (such as, e.g., magnesium and calcium salts). For example, tartrate salts of the compounds of the invention may be included in the pharmaceutical compositions. Furthermore, the compounds of the invention may be present as a hydrate or hemihydrate (of the compound or of its salt).

The compositions can formulated in solid (e.g., powder, tablets), liquid (e.g., aqueous or nonaqueous solutions, dispersions, suspensions or emulsions) or other forms.

Examples of suitable aqueous and nonaqueous carriers, diluents, solvents or vehicles include water (e.g., pyrogen-free water), ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. These compositions may also contain adjuvants, antibacterial and antifungal agents, flavoring agents, biodegradable polymers, etc.

The pharmaceutical compositions of this invention can be administered to mammals (e.g., humans, rodents, etc.) in any suitable way including, e.g., orally, parenterally, intracisternally, intraperitoneally, topically, etc. The parenteral administration includes intravenous, intramuscular, intraperitoneal, intrasternal, subcutaneous and intraarticular injection/infusion. The inhibitory compounds may also be administered as prodrugs that are metabolized into active compound upon administration.

The dose of a GSL synthesis inhibitor will vary depending on the subject and upon the particular route of administration used. Dosages may range from 0.1 to 500 mg/kg body weight per day. In one embodiment, the dosing range is 1-20 mg/kg/day. The GSL inhibitor may be administered continuously or at specific timed intervals. For example, the GSL inhibitor may be administered 1, 2, 3, or 4 times per day, such as, e.g., a daily or twice-daily formulation. Commercially available assays may be employed to determine optimal dose ranges and/or schedules for administration. Assays for measuring blood glucose levels are commercially available (e.g., OneTouch® Uitra®, Lifescan, Inc., Milpitas, Calif.). Kits to measure human insulin levels are also commercially available (Linco Research, Inc., St. Charles, Mo.).

Effective doses may be extrapolated from dose-response curves obtained from animal models. In general, suitable animal models include (1) genetic models such as, e.g., the ob/ob mouse, fa/fa (Zucker) rat, or db/db mouse; (2) overnutrition models, in which animals are fed, e.g., a high sucrose/fructose diet or a high fat diet; (3) the methionine-choline diet deficiency model, which develops steatosis and in, some strains, fibrosis; and (4) transgenic models, such as mice that overexpress the transcription factor SREBP-1 that governs lipid synthesis.

The use of animal models for fatty liver disease is described in the Examples infra. Other animal models are known in the art and are described in, e.g., Koteish et al., *Semin. Liver Dis.* 21:89-104 (2001); Masuzaki et al., *Science* 294:2166-2170 (2001); Lu et al., *Proc. Natl. Acad. Sci, U.S.A.* 98:5560-5565 (2001); Paterson et al., *Proc. Natl. Acad. Sci. U.S.A.* 101:7088-7093 (2004); Farrell, "Animal models of steatosis" in *Fatty Liver Disease: NASH and Related Disorders*, Farrell et al., eds. Blackwell Publishing Ltd., Malden, Mass., 2005; Kirsch et al., J. Gastroenter. Hepatol. 18:1272-1282 (2003); Sahai et al., *Am. J. Physiol. Gastrointest. Liver Physiol.* 287:G1035-1043 (2004); and Lieber et al., *Am. J. Clin. Nutr.* 79:502-509 (2004).

Therapeutically effective dosages achieved in one animal model can be converted for use in another animal, including humans, using conversion factors known in the art (see, e.g., Freireich et al., *Cancer Chemother. Reports* 50:219-244 (1996), Schein et al., *Clin. Pharmacol. Ther.* 11:3-40 (1970), and Table 2 below for equivalent surface area dosage factors).

TABLE 2

| To: | From: | | | | |
| --- | --- | --- | --- | --- | --- |
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

V. Combination Therapy

The invention also contemplates combination therapies for treating liver conditions associated with hepatic lipid deposits. The combination therapy may comprise any of the compounds described herein and at least one other compound suitable for treating a liver condition associated with hepatic lipid deposits, or an underlying condition, such as, e.g., diabetes, metabolic syndrome, or alcoholism.

For example, a GSL synthesis enzyme inhibitor (such as, e.g., a compound of Formula I) may be administered in combination with one or more insulin-sensitizing agents, such as, e.g., biguanides, such as, e.g., metformin (Glucophage®; Bristol-Myers Squibb Company; Princeton, N.J.); thiazolidinediones such as, e.g., pioglitazone (Actosr®; Takeda Pharmaceutical Company Ltd., Lincolnshire, Ill.), rosiglitazone (Avandia®; GlaxoSmithKline, Upper Merrian, Pa.); and leptin. A GSL synthesis inhibitor may be administered in combination with one or more other examples of compounds used to treat type II diabetes including, but not limited to, α-glucosidase inhibitors such as miglitol (Giyset®; Pharmacia, New York, N.Y.); insulin (Novolin®, Novolog®; Velosulin®, Novo Nordisk A/S); meglitinides such as repaglinide (Prandin®; Novo Nordisk, Princeton, N.J.) and nateglinide (Starlix®; Novartis Pharmaceuticals, Cambridge, Mass.); sulfonylureas such as glyburide (Orinase®, Tolinase®, Micronase®, Glynase®; Pharmacia Corp., New York, N.Y.) (Diabeta®, Amaryl®; Aventis, Bridgewater, N.J.), and chlorpropamide (Diabinese®, Glucotrol®, Glucotrol XL®; Pfizer, New York, N.Y.); and combination drugs such as Avandamet® (GlaxoSmithKline, Upper Merrian, Pa.).

A GSL synthesis enzyme inhibitor may be administered in combination with one or more antioxidants, such as, e.g., betaine, histamine, vitamin E, lazaroids (21-aminosteroids), N-acetylcysteine, or S-adenosyl methionine. Alternatively, a GM3 synthesis inhibitor may be administered in combination with one or more lipid-lowering or weight loss agents such as, e.g., gemfibrozil (Lopid®; Parke-Davis, New York, N.Y.), orlistat (Xenical®; Roche Laboratories, Inc., Nutley, N.J.), pentoxifylline (Trental®; Aventis, Bridgewater, N.J.), ursodeoxycholic acid (ursodiol) (Actigall; Watson Pharma, Inc., Corona, Calif.), and HMG-CoA reductase inhibitors ("statins") including, e.g., atorvastatin (Lipitor®; Parke-Davis, New York, N.Y.).

A GSL synthesis enzyme inhibitor may be administered in combination with one or more cytoprotective agents such as, e.g., taurine, ursodeoxycholic acid. Similarly, a GSL synthesis inhibitor may be administered in combination with one or more compounds used to treat alcoholism such as, e.g., acamprosate (Campral®; Merck KGaA, Darmstadt, Germany); alpha-2 adrenergic agonists such as, e.g., clonidine; anticonvulsants such as, e.g., carbamazepine; barbiturates such as, e.g., phenobarbital, pentobarbital, secobarbital; benzodiazepines, such as, e.g., chlordiazepoxide, diazepam, lorazepam, and oxazepam; beta-adrenergic blockers such as, e.g., propranolol; disulfuram; opioid antagonists such as, e.g., naltrexone (ReVia™; Barr Pharmaceuticals, Pomona, N.Y.); phenothiazines such as, e.g., chlorpromazine, thioridazine; and serotonin specific reuptake inhibitors such as, e.g., citalopram, fluoxetine, and fluvoxamine.

EXAMPLES

Example 1

Reduced Hepatic Steatosis in DIO Mice Treated with Formula XI

Figure 2A:
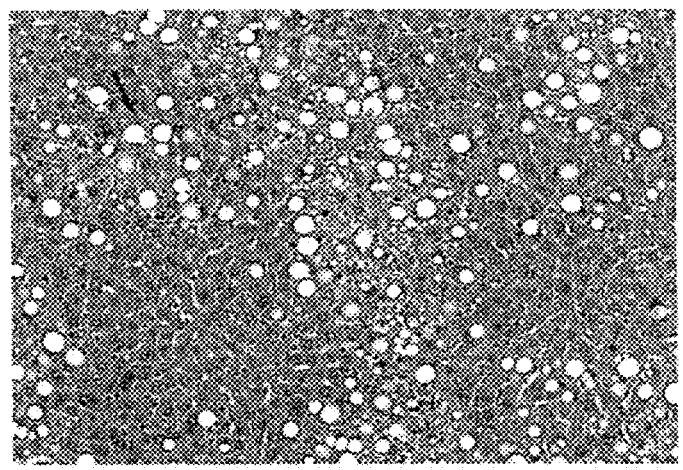
FIGS. 2A-2C are a series of photographs comparing hematoxylin and eosin stained liver sections of (A) diet-induced obese (DIO) C57BL/6 mice treated with water (control), (B) DIO mice treated with D-threo-1-(3',4'-ethylenedioxy)phenyl-2-octanoylamino-3-pyrrolidino-1-propanol (Formula XI), and (C) lean mice treated with water (control). Mice were treated by daily oral gavage for 10 weeks and then sacrificed.
Figure 2B:
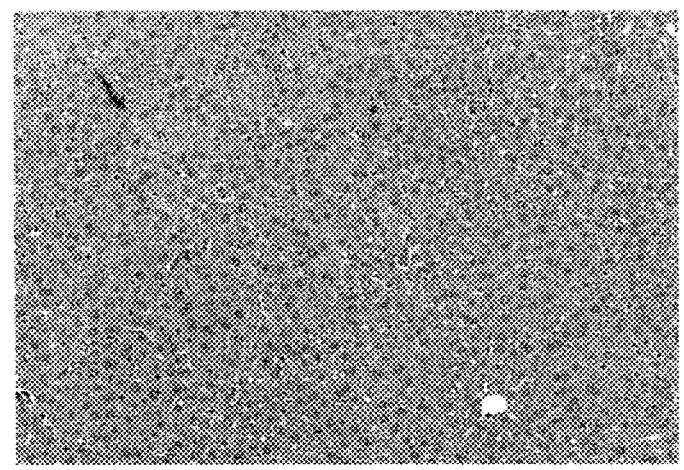
Figure 2C:
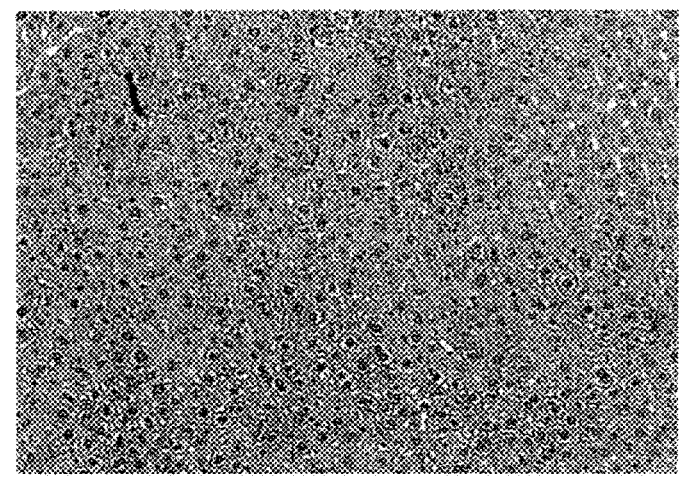

Diet-induced obese (DIO) mice were first generated by placing C57BL/6 mice on a high-fat (45% of kcal) diet (D12451, Research Diets, Inc., New Brunswick, N.J.) for 8 weeks. Obese mice that had elevated glucose and insulin levels were selected and then treated with Formula XI by daily oral gavage (125 mg/kg) or with water as a control. After 10 weeks of treatment, the livers were harvested, sectioned, and stained with hematoxylin and eosin. Large vacuoles were visible throughout the parenchyma of the livers from the water control mice (FIGS. 2A-2C). These vacuoles contain neutral lipid by Oil Red O staining of the liver sections. In contrast, significantly fewer vacuoles were visible in the livers of mice treated with Formula XI, and those vacuoles were appreciably smaller compared to the controls (compare FIG. 2A and FIG. 2C with FIG. 2B). The results indicate that treatment with Formula XI is effective in treating hepatic steatosis in the livers of DIO mice.

Example 2

Treatment of DIO Mice Lowered Triglyceride Levels in the Liver

Figure 3:
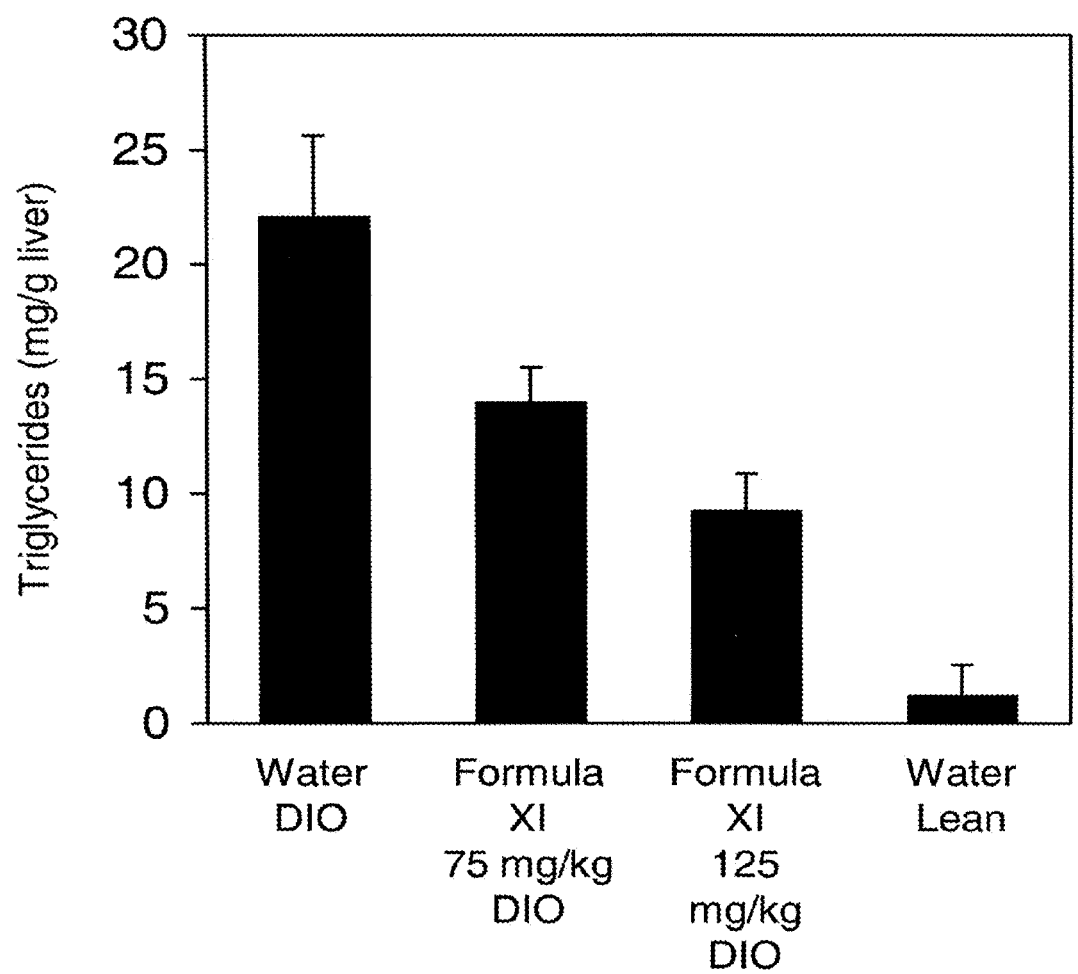
FIG. 3 is a graph comparing the mean levels of liver triglycerides in DIO mice treated with water, DIO mice treated with 75 mg/kg Formula XI, DIO mice treated with 125 mg/kg Formula XI, and lean mice treated with water. Mice were treated by daily oral gavage for 16 weeks and then euthanized. The livers were harvested and homogenized. Triglyceride levels were measured in hepatic lipid extracts. A dose-dependent reduction in total triglyceride levels was observed upon treatment with Formula XI.

DIO mice were generated as described in Example 1 and then treated with Formula XI by daily oral gavage at a dose of 75 or 125 mg/kg. Mice gavaged with water served as the control. After 16 weeks of treatment the livers were harvested and homogenized. The lipids were extracted with methanol:chloroform (4.3:3 v/v) and $CaCl_2$. The extracted lipids were dried and dissolved in dimethylsulfoxide (DMSO). Triglycerides were measured using the Serum Triglyceride Determination kit (Sigma-Aldrich, St. Louis, Mo.) according to the protocol supplied by the manufacturer. The results (FIG. 3) show a dose-dependent reduction in total triglyceride levels as a result of treatment with Formula XI, indicating that treatment with Formula XI is effective in treating hepatic steatosis in the livers of DIO mice.

Example 3

Reduced Liver Weights in DIO Mice Treated with Formula XI

Figure 4:
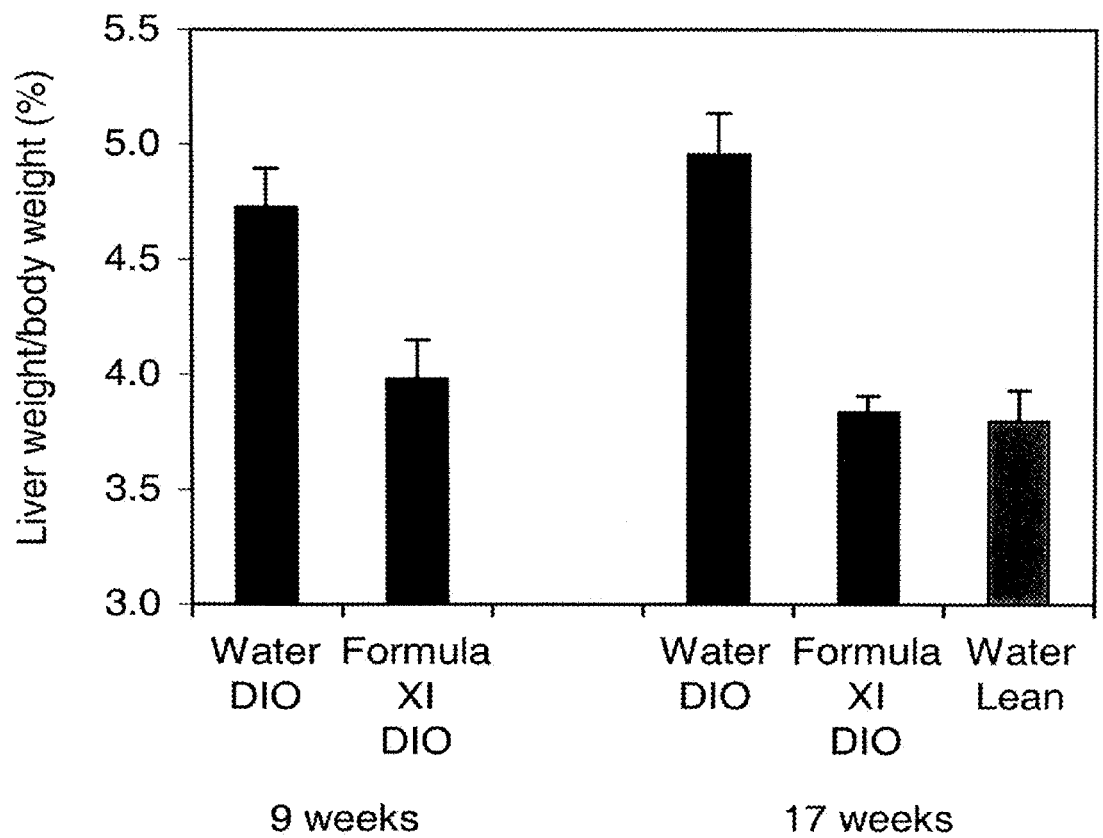
FIG. 4 is a graph comparing the liver weight to body weight ratios of DIO mice treated with water, DIO mice treated with Formula XI, and lean mice treated with water after 9 and 17 weeks of treatment. A reduction in the ratio of liver weight to body weight ratio was observed in DIO mice treated with Formula XI for 9 and 17 weeks.
Figure 5A:
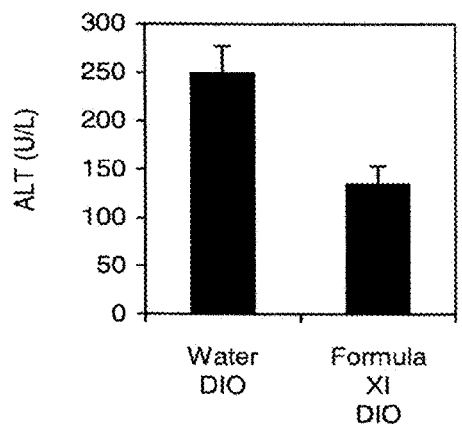
FIGS. 5A-5D are a series of graphs comparing the levels of liver enzymes in DIO mice treated with water and DIO mice treated with Formula XI for 9 weeks.
Figure 5B:
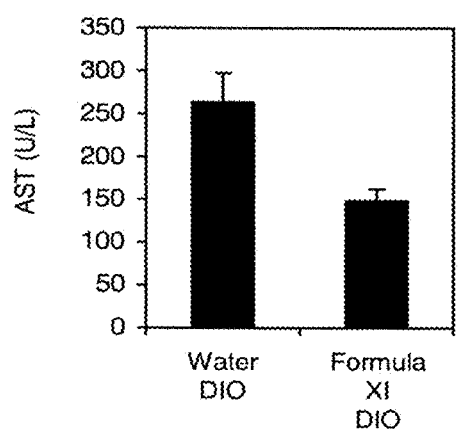
Figure 5C:
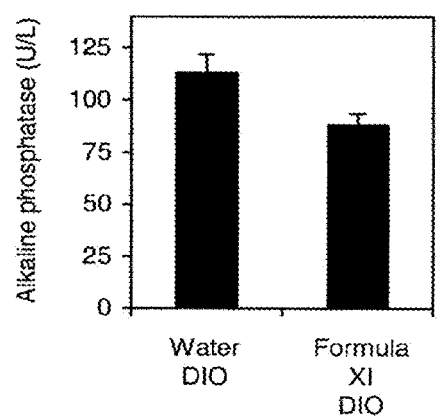
Figure 5D:
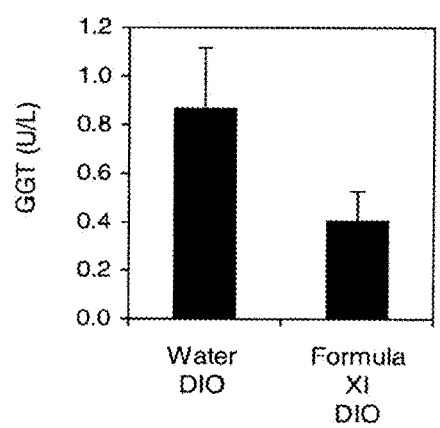

DIO mice were generated as described in Example 1. Mice were maintained on the high-fat diet for an additional 23 weeks (total time on diet 31 weeks). The mice were then treated with Formula XI by daily oral gavage (125 mg/kg/day). Drug treatment did not significantly affect body weight compared to the placebo (water) treated control group. After 9 and 17 weeks of treatment, groups of animals were sacrificed and the livers dissected and weighed. In the DIO mice, the liver weight to body weight ratio was higher than in lean animals. Treatment with Formula XI significantly reduced the liver weights, and after 17 weeks of treatment the liver/body weight ratio was comparable to that of the lean group (FIG. 4). This result suggests that drug treatment could reverse and normalize at least one measure of the gross pathology of the liver in the obese mice.

Example 4

Reduced Markers of Liver Toxicity in DIO Mice Treated with Formula XI

DIO mice were generated as described in Example 1. Mice were maintained on the high-fat diet for an additional 23 weeks (total time on diet 31 weeks). The mice were then treated with Formula XI by daily oral gavage (125 mg/kg/day). Blood was collected after 9 weeks of treatment and markers of liver toxicity were analyzed (IDEXX Laboratories, West Sacramento, Calif.). Lower levels of alanine aminotransferase (ALT), aspartate aminotransferase (AST), alkaline phosphatase, and gamma-glutamyltransferase (GGT) were found in the drug-treated versus placebo-treated control animals (FIGS. 5A-5D). This result indicates that treatment with Formula XI can decrease markers of liver toxicity present in the obese animals fed a high-fat diet, further indicating that treatment with Formula XI is effective in treating hepatic steatosis in the livers of DIO mice.

Example 5

Reduced Hepatic Steatosis in DIO Mice Treated with Gluco-4-Epoxy-4-C-Methyleneglycosyceramide DIO mice are first generated by placing C57BL/6 mice on a high-fat (45% of kcal) diet (D12451, Research Diets, Inc., New Brunswick, N.J.) for 8 weeks. Obese mice having elevated glucose and insulin levels are selected and treated with gluco-4-epoxy-4-C-methyleneglycosyceramide by daily oral gavage (125 mg/kg) or with water as a control. After 10 weeks of treatment, the condition of the mice is evaluated. It is expected that the treatment will result in treatment of the FLD in the mice as determined by one or more of the following:

(a) reduction of lipid deposits (e.g., as described in Example 1 or Example 2),
(b) reduction of liver weight (e.g., as described in Example 3), and
(c) reduction in the liver toxicity markers (e.g., as described in Example 4).

Example 6

Reduced Liver Weights in Ob/Ob Mice Treated with Formula X

Figure 6:
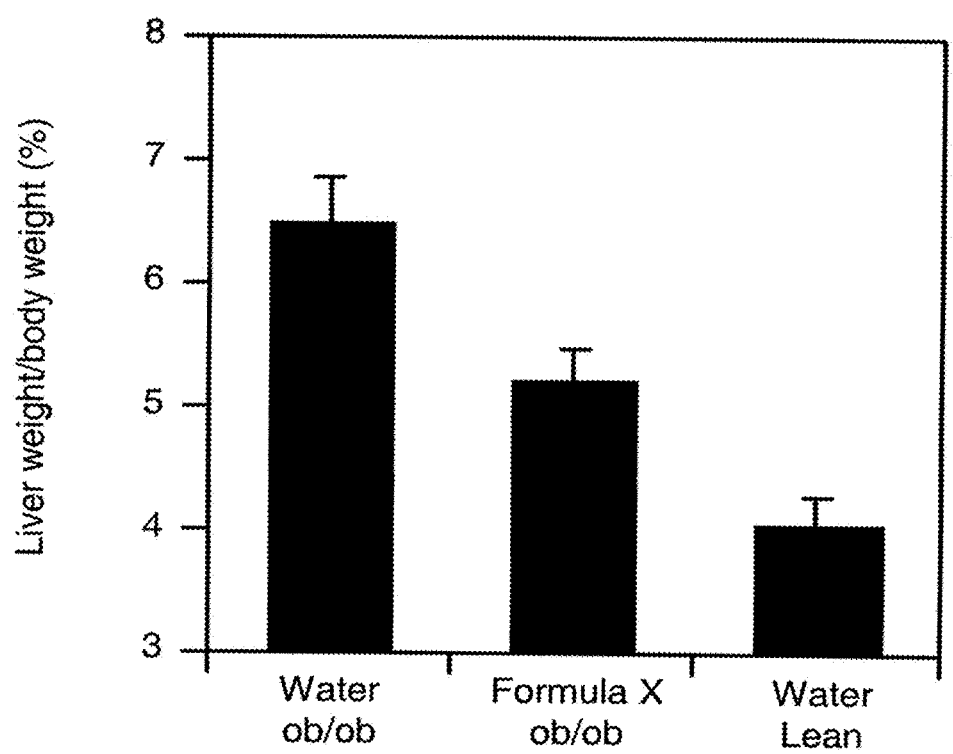
FIG. 6 is a graph comparing the liver weight to body weight ratios of ob/ob mice treated with water, ob/ob mice treated with Formula X, and lean mice treated with water after 6 weeks of treatment. A reduction in the ratio of liver weight to body weight ratio was observed in ob/ob mice treated with Formula X for 6 weeks.
Figure 7A:
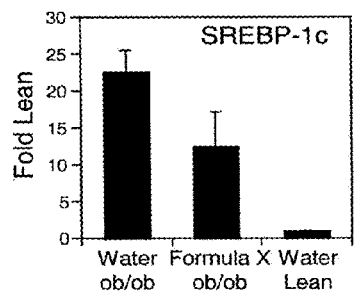
FIGS. 7A-G are a series of graphs comparing the expression of hepatic genes involved in lipogenesis, gluconeogenesis, inflammation, and fibrosis in ob/ob mice treated with water, ob/ob mice treated with Formula X, and lean mice treated with water after 6 weeks of treatment.
Figure 7B:
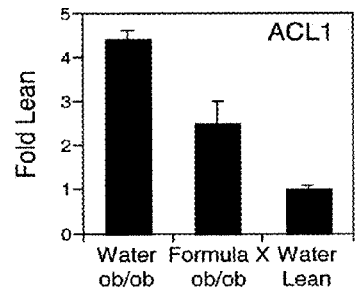
Figure 7C:
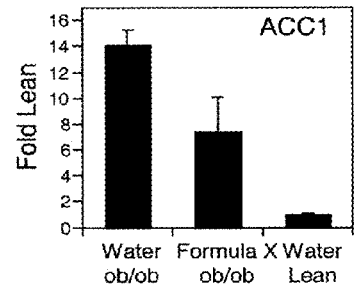
Figure 7D:
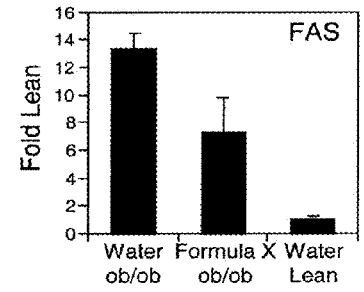
Figure 7E:
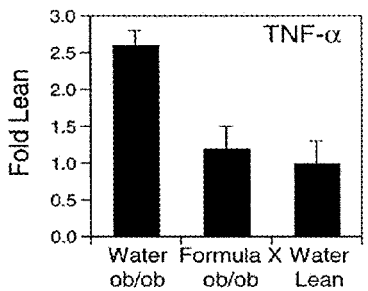
Figure 7F:
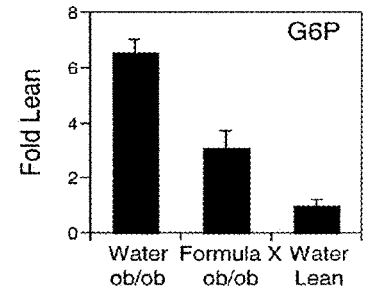
Figure 7G:
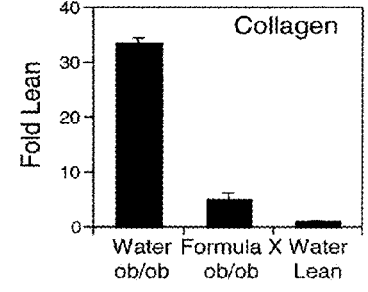

Male ob/ob mice were obtained from the Jackson Laboratories (Bar Harbor, Me.). These mice, being deficient in leptin, are hyperphagic and rapidly become obese. Severe hepatic steatosis is a characteristic of this model. Beginning at 7 weeks of age the mice were treated with Formula X by daily oral gavage (dosed 2× per day at 60 mg/kg/dose or 120 mg/kg/day). Drug treatment did not significantly affect body weight compared to the placebo (water) treated control group (data not shown). After 6 weeks of treatment, the animals were sacrificed and the livers dissected and weighed. In the placebo treated ob/ob mice, the liver weight to body weight ratio was higher than in lean animals (FIG. 6). Treatment with Formula X significantly reduced the liver weights. This result indicates that drug treatment could reduce one measure of the gross pathology of the liver in the obese mice. N=6-8 mice per group.

Example 7

Reduced Expression of Hepatic Genes Involved in Lipogenesis, Gluconeogenesis, Inflammation, and Fibrosis in Ob/Ob Mice Treated with Formula X The ob/ob mice, beginning at 7 weeks of age, were treated with Formula X by daily oral gavage (dosed 2× per day at 60 mg/kg/dose, or 120 mg/kg/day) for 6 weeks. The mice were sacrificed and total RNA was purified from the livers for quantitative RT-PCR (FIG. 7) of sterol regulatory element binding protein 1c (SREBP-1c), acid citrate lyase 1 (ACL1), acetyl coenzyme A carboxylase 1 (ACC1), fatty acid synthase (FAS), tumor necrosis factor 1 alpha (TNF-α), glucose 6-phosphatase (G6P), and procollagen type 1 (collagen). Data were normalized to 18S ribosomal RNA and expressed as fold Lean levels, and indicate that drug treatment reduced the expression of genes involved in lipogenesis (SREBP-1c, ACL1, ACC1, FAS), gluconeogenesis (G6P), inflammation (TNF-α), and fibrosis (Collagen).

All references cited herein are incorporated herein by reference in their entirety. To the extent publications and patents or patent applications incorporated by reference contradict the disclosure contained in the specification, the specification is intended to supersede any such contradictory material.

All numbers expressing quantities of ingredients, reaction conditions, and so forth used in the specification and claims are to be understood as approximate and may vary depending upon the desired properties sought to be obtained. It is intended that the specification and examples be considered as exemplary only, with a true scope and spirit of the invention being indicated by the following claims.

The invention claimed is:

1. A method of treating a fatty liver disease by inhibiting glucosphingolipid synthesis in a mammal in need of the treatment, comprising administering to the mammal an effective amount of a compound of formula I:

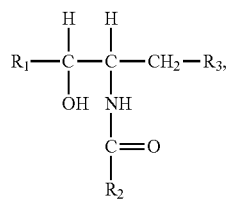

Formula I or a pharmaceutically acceptable salt thereof, wherein $R_1$ is chosen from substituted and unsubstituted aryl; $R_2$ is chosen from substituted and unsubstituted alkyl; and $R_3$ is chosen from substituted and unsubstituted tertiary cyclic amino, wherein the mammal is human.

2. The method of claim 1, wherein the mammal is diagnosed with fatty liver disease.

3. The method of claim 2, wherein the mammal is diagnosed with nonalcoholic steatohepatitis, hepatic fibrosis, or hepatic cirrhosis.

4. The method of claim 1, wherein the mammal is at risk for developing fatty liver disease.

5. The method of claim 1, wherein the treatment results in one or more of the following:
  a. a reduction in serum levels of at least one hepatic enzyme chosen from alanine aminotransferase, aspartate aminotransferase, γ-glutamyltransferase, and alkaline phosphatase; and
  b. a decrease in hepatic lipid deposits.

6. The method of claim 1, wherein the glucosphingolipid whose synthesis is inhibited is chosen from glucosylceramide, gangliosides, globo-series glucosphingolipids, neo-lacto-series glucosphingolipids, isoglobo-series glucosphingolipids, and muco-series glucosphingolipids.

7. The method of claim 6, wherein the glucosphingolipid is a ganglioside.

8. The method of claim 7, wherein the ganglioside is an a-series ganglioside, a b-series ganglioside, a c-series ganglioside, or an o-series ganglioside.

9. The method of claim 8, wherein the ganglioside is an a-series ganglioside.

10. The method of claim 9, wherein the a-series ganglioside is the ganglioside GM3.

11. The method of claim 10, wherein the ganglioside GM3 synthesis is inhibited by inhibiting activity or expression of one of more GM3 synthesis enzymes selected from the group consisting of (a) glucosylceramide synthase, (b) lactosylceramide synthase, and (c) GM3 synthase.

12. The method of claim 11, wherein the ganglioside GM3 synthesis is inhibited by administering to the mammal a therapeutically effective amount of a composition comprising an inhibitor of glucosylceramide synthase enzymatic activity.

13. The method of claim 12, wherein the composition is administered orally.

14. The method of claim 13, wherein the inhibitor of glucosylceramide synthase enzymatic activity is a substrate analog of a glucosylceramide synthase.

15. The method of claim 1, wherein $R_2$ is substituted by hydroxyl, alkoxy or aryloxy.

16. The method of claim 1, wherein $R_2$ is $C_2$-$C_4$ alkyl substituted by optionally substituted alkoxy or optionally substituted aryloxy.

17. The method of claim 16, wherein $R_2$ is $C_2$ alkyl substituted by optionally substituted aryloxy.

18. The method of claim 17, wherein $R_2$ is $C_2$ alkyl substituted by 4-methoxyphenoxy.

19. The method of claim 1, wherein $R_2$ comprises at least 7 carbon atoms.

20. The method of claim 1, wherein $R_2$ is chosen from substituted and unsubstituted $C_7$-$C_{18}$ alkyl.

21. The method of claim 20, wherein $R_2$ is chosen from substituted and unsubstituted $C_7$ alkyl.

22. The method of claim 21, wherein $R_2$ is 1-(1-hydroxyheptyl) or 1-(6-hydroxyheptyl).

23. The method of claim 20, wherein $R_2$ is chosen from substituted and unsubstituted $C_8$ alkyl.

24. The method of claim 23, wherein $R_2$ is 1-(1-hydroxyoctyl) or 1-(7-hydroxyoctyl).

25. The method of claim 1, wherein $R_3$ is pyrrolidino, and $R_2$ is $C_2$ alkyl.

26. The method of claim 1, wherein $R_3$ is pyrrolidino, and $R_2$ is $C_7$ alkyl.

27. The method of claim 1, wherein $R_3$ is pyrrolidino, and $R_2$ is $C_8$ alkyl.

28. The method of claim 1, wherein the compound of Formula I is 1-(1,4-benzodioxan-6-yl)-2-nonanoylamino-3-pyrrolidino-1-propanol or a pharmaceutically acceptable salt thereof.

29. The method of claim 28, wherein the compound of Formula I is 1(R)-(1,4-benzodioxan-6-yl)-2(R)-nonanoylamino-3-pyrrolidino-1-propanol, or a pharmaceutically acceptable salt thereof.

30. The method of claim 1, wherein the compound of Formula I is 1-(1,4-benzodioxan-6-yl)-2-(4-methoxyphenoxy)propanoylamino-3-pyrrolidino-1-propanol, or a pharmaceutically acceptable salt thereof.

31. The method of claim 30, wherein the compound of Formula I is 1(R)-(1,4-benzodioxan-6-yl)-2(R)-(4-methoxyphenoxy)propanoylamino-3-pyrrolidino-1-propanol, or a pharmaceutically acceptable salt thereof.

32. The method of claim 1, wherein the compound of Formula I is in the form of a pharmaceutically acceptable salt.

33. The method of claim 32, wherein the pharmaceutically acceptable salt is tartrate.

34. The method of claim 1, further comprising administering to the subject at least one compound selected from the group consisting of an α-glucosidase inhibitor, a biguanide, insulin, a meglitinide, a sulfonylurea, a thiazolidinedione, an antioxidant, a lipid-lowering agent, a weight-loss agent, a cytoprotective agent, an alpha-2 adrenergic agonist, an anticonvulsant, a barbiturate, a benzodiazepine, a beta-adrenergic blocker, disulfiram, an opioid antagonist, a phenothiazine, and a serotonin reuptake inhibitor.

* * * * *